United States Patent
Brogan et al.

(10) Patent No.: US 9,689,083 B2
(45) Date of Patent: Jun. 27, 2017

(54) TSV BATH EVALUATION USING FIELD VERSUS FEATURE CONTRAST

(71) Applicant: Lam Research Corporation, Fremont, CA (US)

(72) Inventors: Lee Brogan, Tualatin, OR (US); Steven T. Mayer, Lake Oswego, OR (US); Matthew Thorum, Portland, OR (US); Joseph Richardson, Sherwood, OR (US); David W. Porter, Sherwood, OR (US); Haiying Fu, Camas, WA (US)

(73) Assignee: Lam Research Corporation, Fremont, CA (US)

( * ) Notice: Subject to any disclaimer, the term of this patent is extended or adjusted under 35 U.S.C. 154(b) by 271 days.

(21) Appl. No.: 14/275,750

(22) Filed: May 12, 2014

(65) Prior Publication Data

US 2014/0367279 A1 Dec. 18, 2014

Related U.S. Application Data

(60) Provisional application No. 61/835,418, filed on Jun. 14, 2013.

(51) Int. Cl.
C25D 21/12 (2006.01)

(52) U.S. Cl.
CPC .................................. C25D 21/12 (2013.01)

(58) Field of Classification Search
None
See application file for complete search history.

(56) References Cited

U.S. PATENT DOCUMENTS

| 4,324,621 | A | 4/1982 | Kerby |
|---|---|---|---|
| 5,196,096 | A | 3/1993 | Chang et al. |
| 6,458,262 | B1 | 10/2002 | Reid et al. |
| 6,627,066 | B1 | 9/2003 | Isayama et al. |
| 6,740,220 | B1 | 5/2004 | Medeiros et al. |
| 6,740,221 | B2 | 5/2004 | Cheung et al. |

(Continued)

FOREIGN PATENT DOCUMENTS

| CA | 988879 | 5/1976 |
|---|---|---|
| CN | 1764746 A | 4/2006 |

(Continued)

OTHER PUBLICATIONS

US Office Action, dated Mar. 29, 2012, issued in U.S. Appl. No. 12/462,354.

(Continued)

*Primary Examiner* — Matthew Martin
*Assistant Examiner* — Steven E Rosenwald
(74) *Attorney, Agent, or Firm* — Weaver Austin Villeneuve & Sampson LLP

(57) ABSTRACT

The embodiments herein relate to methods and apparatus for determining whether a particular test bath is able to successfully fill a feature on a substrate. In various cases, the substrate is a semiconductor substrate and the feature is a through-silicon-via. Generally, two experiments are used: a first experiment simulates the conditions present in a field region of the substrate during the fill process, and the second experiment simulates the conditions present in a feature on the substrate during the fill process. The output from these experiments may be used with various techniques to predict whether the particular bath will result in an adequately filled feature.

24 Claims, 10 Drawing Sheets

(56) References Cited

U.S. PATENT DOCUMENTS

| | | |
|---|---|---|
| 6,827,839 B2 | 12/2004 | Sonnenberg et al. |
| 7,144,488 B2 | 12/2006 | Binstead et al. |
| 7,186,326 B2 | 3/2007 | Shalyt et al. |
| 7,232,513 B1 | 6/2007 | Webb et al. |
| 7,270,733 B2 | 9/2007 | Wikiel et al. |
| 7,405,163 B1 | 7/2008 | Drewery et al. |
| 7,449,098 B1 | 11/2008 | Mayer et al. |
| 7,449,099 B1 | 11/2008 | Mayer et al. |
| 7,531,079 B1 | 5/2009 | Mayer et al. |
| 7,560,016 B1 | 7/2009 | Mayer et al. |
| 7,776,741 B2 | 8/2010 | Reid et al. |
| 7,799,200 B1 | 9/2010 | Mayer et al. |
| 7,947,163 B2 | 5/2011 | Mayer et al. |
| 8,268,154 B1 | 9/2012 | Mayer et al. |
| 8,372,258 B2 | 2/2013 | Willey et al. |
| 8,500,983 B2 | 8/2013 | Ponnuswamy et al. |
| 9,309,605 B2 | 4/2016 | Mayer |
| 2002/0074244 A1 | 6/2002 | Sonnenberg et al. |
| 2004/0046121 A1 | 3/2004 | Golden et al. |
| 2005/0183958 A1 | 8/2005 | Wikiel et al. |
| 2008/0264801 A1 | 10/2008 | West et al. |
| 2009/0057151 A1 | 3/2009 | Shalyt et al. |
| 2009/0139873 A1 | 6/2009 | Wang et al. |
| 2011/0025338 A1 | 2/2011 | Willey et al. |
| 2011/0284386 A1 | 11/2011 | Willey et al. |
| 2013/0161203 A1 | 6/2013 | Mayer |
| 2016/0186356 A1 | 6/2016 | Mayer |

FOREIGN PATENT DOCUMENTS

| | | |
|---|---|---|
| CN | 2828067 Y | 10/2006 |
| CN | 1957115 A | 5/2007 |
| CN | 101004401 A | 7/2007 |
| CN | 100337111 C | 9/2007 |
| CN | 102097347 A | 6/2011 |
| CN | 103014823 A | 4/2013 |
| CN | 103035503 A | 4/2013 |
| JP | 2001152398 A | 6/2001 |
| JP | 2004217997 A | 8/2004 |
| JP | 2005-504965 | 2/2005 |
| JP | 2005171347 A | 6/2005 |
| KR | 10-2002-0060716 | 7/2002 |
| KR | 10-2006/0074593 | 7/2006 |
| KR | 10-2007-0012525 | 1/2007 |
| TW | 457544 B | 10/2001 |
| TW | 562877 B | 11/2003 |
| TW | 200409916 A | 6/2004 |
| TW | I226439 B | 1/2005 |
| WO | WO 03/279779 | 4/2003 |
| WO | WO 2006/110437 | 10/2006 |
| WO | WO 2011/017197 | 2/2011 |
| WO | WO 2013/090295 A1 | 6/2013 |

OTHER PUBLICATIONS

US Notice of Allowance, dated Oct. 9, 2012, issued in U.S. Appl. No. 12/462,354.
PCT International Search Report and Written Opinion, dated Apr. 22, 2011, issued in PCT/US2010/043764.
PCT International Preliminary Report on Patentability and Written Opinion, dated Feb. 7, 2012, issued in PCT/US2010/043764.
Chinese First Office Action and Search Report dated Nov. 14, 2013, issued in CN 201080034658.4.
Chinese Second Office Action dated May 20, 2014, issued in CN 201080034658.4.
Taiwan Notice of Allowance and Search Report dated Oct. 24, 2013 issued in TW 099125629.
PCT International Preliminary Report on Patentability and Written Opinion, dated Jun. 17, 2014, issued in PCT/US2012/069016.
International Search Report and Written Opinion, dated Mar. 28, 2013, issued in Application No. PCT/US2012/069016.
U.S. Appl. No. 13/572,483, filed Aug. 10, 2012, and titled "Selective Electrochemical Accelerator Removal," Mayer, et al.
US Notice of Allowance, dated Dec. 15, 2015, issued in U.S. Appl. No. 13/711,254.
Chinese First Office Action dated Apr. 28, 2016 issued in CN 201410268283.8.
Korean Office Action dated May 18, 2016 issued in KR 10-2012-7004328.
CN Office Action dated Jan. 20, 2017, issued in Application No. 201410268283.8.
U.S. Application Titled "TSV Bath Evaluation Using Field Versus Feature Contrast," filed May 9, 2017, U.S. Appl. No. 15/590,718.

FIG. 9A
Table 1 – Technique 1

| Electrode Diameter (mm) | RPM | Time (s) | $CD_{th}$ (mA/cm²) | Failed Bath 1 | Failed Bath 2 | Failed Bath 3 | Successful Bath 4 |
|---|---|---|---|---|---|---|---|
| 5 | 0 | 300 | 65 | 7.689 | 56.247 | 38.418 | 70.259 |
| 5 | 2500 | 600 | 45 | 9.093 | 42.332 | 24.071 | 46.949 |
| 0.433 | 0 | 60 | 250 | 29.439 | 210.038 | 134.409 | 256.122 |
| 0.433 | 2500 | 360 | 140 | 26.617 | 130.396 | 105.488 | 157.358 |

FIG. 9B
Table 2 – Technique 2

| Electrode Diameter (mm) | RPM | $CD_{th}$ (mA/cm²) | $t_{th}$ (s) | Failed Bath 1 (s) | Failed Bath 2 (s) | Failed Bath 3 (s) | Successful Bath 4 (s) |
|---|---|---|---|---|---|---|---|
| 5 | 0 | 63 | 360 | 2.141 | 2.171 | 2.141 | 600 |
| 5 | 2500 | 50 | 360 | 3.371 | 320.671 | 3.171 | 535.171 |
| 0.433 | 0 | 190 | 240 | 2.611 | 4.111 | 3.111 | 265.611 |
| 0.433 | 2500 | 140 | 360 | 4.611 | 2.081 | 129.611 | 403.111 |

FIG. 9C
Table 3 – Technique 3

| Electrode Diameter (mm) | RPM | Time ($t_1 - t_2$) (s) | $C_{th}$ (charge/cm²) | Failed Bath 1 (charge/cm²) | Failed Bath 2 (charge/cm²) | Failed Bath 3 (charge/cm²) | Successful Bath 4 (charge/cm²) |
|---|---|---|---|---|---|---|---|
| 5 | 0 | 30 - 240 | 140 | 24.399 | 112.677 | 80.086 | 145.289 |
| 5 | 2500 | 30 - 240 | 140 | 27.213 | 113.252 | 73.357 | 143.29 |
| 0.433 | 0 | 30 - 240 | 450 | 54.289 | 439.075 | 259.812 | 475.3 |
| 0.433 | 2500 | 30 - 240 | 450 | 60.413 | 389.661 | 276.986 | 530.765 |

TSV BATH EVALUATION USING FIELD VERSUS FEATURE CONTRAST

CROSS REFERENCE TO RELATED APPLICATION

This application claims benefit of priority to U.S. Provisional Application No. 61/835,418, filed Jun. 14, 2013, and titled "TSV BATH EVALUATION USING FIELD VERSUS FEATURE CONTRAST," which is herein incorporated by reference in its entirety and for all purposes.

BACKGROUND

Damascene processing is a method for forming metal lines on integrated circuits. It is often used because it requires fewer processing steps than other methods and offers a high yield. Through-Silicon-Vias (TSVs) are sometimes used in conjunction with Damascene processing to create three-dimensional (3D) packages and 3D integrated circuits by providing interconnection of vertically aligned electronic devices through internal wiring. Such 3D packages and 3D integrated circuits may significantly reduce the complexity and overall dimensions of a multi-chip electronic circuit. Conductive routes on the surface of an integrated circuit formed during Damascene processing or in TSVs are commonly filled with copper.

A TSV is a vertical electrical connection passing completely through a silicon wafer or die. A typical TSV process involves forming TSV holes and depositing a conformal diffusion barrier and conductive seed layers, followed by filling of the TSV holes with a metal. Copper is typically used as the conductive metal in TSV fill as it supports the high current densities experienced at complex integration, such as for 3D packages and 3D integrated circuits. Copper also supports high device speeds. Furthermore, copper has good thermal conductivity and is available in a highly pure state.

TSV holes typically have high aspect ratios which makes void-free deposition of copper into such structures a challenging task. Chemical vapor deposition (CVD) of copper requires complex and expensive precursors, while physical vapor deposition (PVD) often results in voids and limited step coverage. Electroplating is a more common method of depositing copper into TSV structures; however, electroplating also presents a set of challenges because of the TSV's large size and high aspect ratio.

In a typical TSV electrofilling process, the substrate is negatively electrically biased and is contacted with a plating solution which generally includes copper sulfate or copper methane sulphonate as a source of copper ions, as well as sulfuric acid or methane sulfonic acid for controlling conductivity, along with chloride ions and organic additives in various functional classes, known as suppressors, accelerators and levelers. The concentration of these plating bath components typically changes over the course of processing as the components are incorporated into the plated substrate, degrade over time, etc. As such, in order to achieve consistently satisfactory fill results it is necessary to monitor the composition of the bath over time. In this way, when the concentration of a plating bath additive is found to be too low, for example, appropriate steps can be taken to increase the concentration of that additive in the bath.

Widely used conventional methods for monitoring plating baths typically utilize scanning voltammetric coulometry, electrochemical titrations, spectroscopic methods (e.g., visible, IR and UV solution analysis), and various forms of HPLC to independently attempt to evaluate the concentration of various known bath components (e.g., metal, acid, and each additive) at concentrations close to the target operating concentrations. For example, in the voltammetric coulometry method, a platinum rotating disk electrode (RDE) is used as a working electrode. A signal is generated by integrating the charge passed during the anodic stripping wave of a cyclic voltammogram. Typically, a series of similar experiments are performed where the concentration of a target species in solution is modified. The solution will generally be largely insensitive to the concentration of other (non-target) bath species.

As one example, a surface that is more accelerated will exhibit faster copper plating, and the system will pass more charge during stripping. As such, a solution having an excess concentration of suppressor and a relatively higher concentration of accelerator will tend to show larger deposition and stripping charge than a solution having relatively less accelerator. As such, this type of solution may be used to measure the concentration of accelerator in solution by comparing the electrochemical response of the solution to the responses seen in a series of solutions having known levels of accelerator. The concentrations of accelerator and suppressor are determined using standard addition methods in which the ability of the plating bath to accelerate or suppress plating is evaluated relative to standard solutions. Other methods can also be used, but they likewise do not indicate the potential of the combined species in the bath in its current state (having both known/recognized and unrecognized species present). These conventional methods are able to provide reasonably accurate determinations regarding the total amount of accelerator or suppressor in the bath (though in some cases breakdown products may interfere, leading to a false signal). However, although the conventional methods are usually fairly accurate, they are not sufficiently precise to enable detection of small perturbations in the bath chemistry (e.g., the formation of very low levels of plating bath breakdown products), and they do not indicate the presence of unrecognized, potentially process poisoning or other deleterious species. These composition perturbations, though relatively small, can lead to failure in the TSV fill process.

For example, the breakdown of a small amount of accelerator can produce products with incomplete fills. Further, the loss of certain moieties responsible for maintaining suppression over long time intervals can result in incomplete fills. The addition of trace amounts of leveler moieties can likewise result in incomplete TSV fills. Further, the presence of various unrecognized materials can lead to fill failure. Each of these problems can occur at concentration changes/levels that are not detectable by conventional methods. In other words, the TSV fill process is more sensitive to changes in the bath composition than the conventional composition monitoring methods are. Thus, the conventional metrology methods are unable to accurately predict whether a particular plating bath will produce an acceptable bottom-up fill result, and can lead to the production of sub-standard devices or even the complete loss of valuable substrates.

More robust control over the quality of the filling process within an individual wafer and over the course of plating multiple wafers on a plating tool is desired. Specifically, a method that indicates whether a particular plating bath will (or will not) meet a defined electroplating specification (e.g., produce a successful bottom-up fill), that does not rely on the specifics of any particular additive constituent, additive concentration or compositions, and that does not require individually testing for the presence of different species, is desired. The disclosed techniques meet these criteria, and in particular, can be performed without knowledge of the identity of the specific species that may be present in the solution.

SUMMARY

Certain embodiments herein relate to methods and apparatus for determining whether an electroplating solution is capable of meeting a defined electroplating specification. In certain cases the specification may relate to producing an acceptable bottom-up fill result in a recessed feature of a substrate. In one aspect of the embodiments herein, a method includes performing a current-controlled experiment designed to closely approximate a set of plating conditions used in a target electroplating process to obtain a potential trace output, wherein the current-controlled experiment is performed with a metal plated electrode in a solution of interest (a test solution), using the potential output of the current-controlled experiment to designate a potential profile to be used in a potential-controlled experiment, performing the potential-controlled experiment using the designated potential profile to obtain a current density trace output, wherein the potential-controlled experiment is performed with a second metal plated electrode in the solution of interest, and wherein the second metal plated electrode has a substantially fully accelerated surface, and analyzing one or more of the potential trace output and current density trace output to predict whether the solution of interest is capable of successfully filling a recessed feature on a substrate.

In some cases, the metal plated electrode and the second metal plated electrode are the same electrode. The metal plated electrode may be cleaned before it is used in the potential-controlled experiment. The cleaning may involve removing metal plated on the electrode surface. In some cases the removal may be accomplished by electrochemical anodization. In other cases the removal may be accomplished through chemical etching of the surface of the metal plated electrode. The surface of the cleaned electrode may be rinsed with water or other cleaning solution.

The second metal plated electrode may be exposed to an accelerator-rich solution to achieve the substantially fully accelerated surface. In some cases, the exposure to accelerator-rich solution may happen as the second metal plated electrode is plated with metal (i.e., during a pre-plating operation). The second metal plated electrode may also be rinsed after it achieves its substantially fully accelerated surface, and prior to use in the potential-controlled experiment.

In some embodiments, the designated potential profile obtained in the current-controlled experiment and used in the potential-controlled experiment is a static profile at, e.g., an average value of the potential trace output during a final period in the current-controlled experiment. In other embodiments, the designated potential profile is a linearly progressed dynamic profile based on a potential trace output during all or a portion (e.g., the final period) in the current-controlled experiment.

The analyzing operation may include analyzing the output of the current-controlled and potential-controlled experiments based on one or more techniques. One analysis technique may include comparing the output of the potential-controlled experiment at a certain time to a threshold value. Another analysis technique may include comparing the time at which the output of the potential-controlled experiment passes a threshold current density, to a threshold time. Another analysis technique may include comparing the amount of charge passed per area (of electrode surface) over a certain timeframe during the potential-controlled experiment to a threshold amount of charge per area. This technique may involve integrating the output of the potential-controlled experiment over a relevant timeframe. Other techniques may be used, as well.

In another aspect of the disclosed embodiments, a method for determining whether an electroplating solution is capable of producing an acceptable bottom-up fill result includes two current-controlled experiments, rather than a current-controlled experiment and a potential-controlled experiment. In this case, the method may include performing a first current-controlled experiment designed to closely approximate a set of plating conditions used in a target electroplating process to obtain a first potential trace output, where the current-controlled experiment is performed with a metal plated electrode in a solution of interest (a test solution), performing a second current-controlled experiment to obtain a second potential trace output, where the second current-controlled experiment is performed with a second metal plated electrode in the solution of interest, where the second metal plated electrode has a substantially fully accelerated surface, and wherein a current density profile applied during the second current-controlled experiment is a current density profile needed to produce complete fill of the recessed features in a timely fashion, and analyzing one or more of the first and second current trace output to predict whether the solution of interest is capable of successfully filling a recessed feature on a substrate.

The technique for analyzing the output of the experiments may involve calculating a ratio of the first potential trace output at time $t_1$ to the second potential trace output at time $t_2$, and comparing it to a threshold ratio. The times ($t_1$ and $t_2$) and the threshold ratio may be determined empirically. The analyzing technique allows for a comparison of the relative polarization of the feature and field regions on the substrate. Where the polarization of the feature is sufficiently small compared to the polarization of the field region at relevant time(s), the plating contrast ratio will be maintained and the fill will complete successfully.

The electrochemical cell used to perform the experiments may include a working electrode, a counter electrode and a reference electrode, which can determine the potential at the working electrode. The counter electrode may be separated from the working electrode by a membrane. In a different embodiment, the counter electrode and working electrode may be contained in separate containers connected by a salt bridge. The electrochemical cell also typically contains a mechanism for measuring and recording an electrochemical response of the system. In some cases, the electrochemical cell used to perform the experiments is included in a multi-station process tool. In various implementations, the electrochemical cell also includes a controller that is designed or configured to perform one or more aspects of the disclosed methods.

In one aspect of the disclosed embodiments, a method of evaluating whether additives in an electroplating bath of interest meet an electroplating specification is provided, the method including: performing a first experiment by: contacting an electrode with the electroplating bath of interest, applying a current density waveform to the electrode, where the current density waveform applied approximates a current density experienced in a field region of a substrate when electroplated in the electroplating bath of interest, and recording a first potential trace output during the first experiment; performing a second experiment by: contacting a second electrode with an acceleration solution including accelerator until the second electrode is substantially fully accelerated, rinsing the acceleration solution from the second electrode, contacting the second electrode with the electroplating bath of interest, applying a second current density waveform or a potential waveform to the electrode, where the second current density waveform or potential waveform approximates the current density or potential experienced within a feature on the substrate when electroplated in the electroplating bath of interest, where a second current density waveform is applied, recording a second potential trace output during the second experiment, and where a potential waveform is applied to the electrode, recording a current trace output during the second experiment; and determining, based on two or more parameters selected from the group consisting of the first potential trace output, the second potential trace output, the current trace output, and calibration data, whether the additives in the electroplating bath meet the electroplating specification.

In some embodiments, the electroplating specification relaters to the capability of the additives in the electroplating bath of interest to fully fill the feature on the substrate through a bottom-up mechanism in an acceptable timeframe. The current density waveform applied during the first experiment may correspond to a current density waveform used for electroplating material on the substrate in a target filling process. In some cases, the current density waveform applied during the first experiment corresponds to a current density waveform used for electroplating material on the semiconductor substrate in a target filling process, as modified by a field current density correction factor.

In some cases, different convective conditions are achieved during each experiment. For instance, a rotation rate of the second electrode during the second experiment may be higher than a rotation rate of the semiconductor substrate during the target filling process. In another example, a temperature of the electroplating bath of interest during the second experiment may be higher than a temperature of the electroplating bath of interest during the target filling process.

The output of the first experiment may have an effect on the second experiment. In one embodiment, the first potential trace output from the first experiment is used to select the potential waveform applied in the second experiment. For example, the potential waveform may be selected based on the potential experienced during a final period of electroplating during the first experiment. In some cases, the potential waveform may be selected based on an average potential of the first potential trace output during a final period of electroplating during the first experiment. In certain other embodiments, the potential trace output from the first experiment may be used to calculate a predicted potential, the predicted potential corresponding to a potential that would be experienced if electroplating were to continue after a final electroplating period in the first experiment, and where the potential waveform in the second experiment is based on the predicted potential. Where the second experiment involves applying a second current density waveform, this second current density waveform may be selected based on a current density to fully fill the feature in the acceptable timeframe.

The electrode and the second electrode may be the same electrode. The method may further include removing material deposited on the electrode during the first experiment before contacting the electrode with the acceleration solution.

The determination of whether the additives in the electroplating bath of interest meet the defined specification may involve one or more of several different analysis options. In some cases, the determining includes comparing a current density at a relevant time from the current density trace output from the second experiment to a threshold current density. In these or other cases, the determining may also include comparing a time at which the current density trace output from the second experiment reaches a threshold current density to a threshold time. In some embodiments, the determining involves integrating the current density trace output from the second experiment between a first time and a second time to calculate a charge density, and comparing the charge density to a threshold charge density. In other cases, the determining may involve calculating a ratio between a potential from the first potential trace output at a first time during the first experiment to a potential from the second potential trace output at a second time during the second experiment, and comparing the ratio to a threshold ratio.

In various embodiments, calibration data is used to make the determination of whether the additives in the electroplating bath meet the electroplating specification. The calibration data may be generated by performing the first and/or second experiment on electrolytes that are known to produce acceptable fill results and electrolytes that are known to produce unacceptable fill results. The calibration data may include one or more of the parameters selected from the group consisting of: a threshold current density, a threshold charge density, a threshold time, and a threshold ratio of potentials.

The acceptable timeframe may vary depending on the size and shape of the feature in question. In various cases, the acceptable timeframe may be about 1 hour or less. The electrode and second electrode may be pre-plated with metal. For instance, the method may further include electroplating metal onto the electrode before contacting the electrode with the electroplating bath of interest in the first experiment, and electroplating metal onto the second electrode before contacting the second electrode with the acceleration solution. In other cases, electroplating metal onto the second electrode may occur while the second electrode is being contacted with the acceleration solution. The acceleration solution may have a concentration of accelerator that is at least about 10 times the concentration of accelerator in the electroplating bath of interest. In some cases, the concentration of accelerator in the acceleration solution may be at least about 100 times the concentration of accelerator in the electroplating bath of interest.

In another aspect of the disclosed embodiments, a method of monitoring the additives in an electroplating bath of interest is provided, the method including: (a) applying a defined current density to a first electrode while in contact with the electroplating bath of interest, where the defined current density represents a current density experienced in a field region of a substrate when electroplated in the electroplating bath of interest, and where the first electrode's surface is not substantially fully accelerated; (b) recording a potential trace output of the first electrode when applying the defined current density; (c) applying a second defined current density or a defined potential to a substantially fully accelerated surface of a second electrode while in contact with the electroplating bath of interest, where the second defined current density or the defined potential represents the current density or potential experienced within a feature on the substrate when electroplated in the electroplating bath of interest; recording a second potential trace output and/or a current density trace output of the second electrode when applying the second defined current density or the defined potential; and (e) determining, based on information contained in one or more of the outputs, whether the additives of the electroplating bath of interest meet a defined electroplating specification.

In a further aspect of the disclosed embodiments, an apparatus for evaluating whether additives in an electroplating bath of interest meet an electroplating specification, the apparatus including: an analysis chamber; one or more inlets for providing to the analysis chamber a test bath solution from an electroplating bath of interest and one or more additional solutions; an outlet for removing fluid from the analysis chamber; a working electrode; a power supply; and a controller having instructions to: (a) perform a first experiment while test bath solution is present in the analysis chamber by applying a defined current density to the working electrode, and recording a potential trace output of the working electrode; (b) contact the working electrode with an acceleration solution for a duration sufficient to substantially fully saturate the working electrode with accelerator; (c) perform a second experiment while test bath solution is present in the analysis chamber by either (i) applying a second defined current density to the working electrode and recording a second potential trace output of the working electrode, or (ii) applying a defined potential to the working electrode and recording a current density trace output; and (d) determine, based on information contained in one or more of the potential trace output, the second potential trace output, the current density trace output, and calibration data, whether the electroplating additives in the electroplating bath of interest meet the electroplating specification.

In some cases, the controller further includes instructions for: prior to (a): flowing a standardized electroplating solution into the analysis chamber and electroplating metal onto the working electrode while the working electrode is in contact with the standardized electroplating solution; removing the standardized electroplating solution from the analysis chamber; and flowing the test bath solution into the analysis chamber. The controller may also have instructions for: after (a) and before (b): removing material electroplated onto the working electrode, and removing the test bath solution from the analysis chamber; and after (b) and before (c): rinsing the working electrode to thereby remove unadsorbed acceleration solution, and flowing test bath solution into the analysis chamber.

Different techniques may be used to remove the electroplated material from the working electrode. In some cases, the instructions for removing material electroplated onto the working electrode include instructions to apply a reverse current to the working electrode to thereby deplate the material. In other cases, the instructions for removing material electroplated onto the working electrode include instructions for flowing a chemical etching solution in the analysis chamber to thereby chemically etch the material from the working electrode.

The instructions in (b) may further include instructions for flowing the acceleration solution in to the analysis chamber to thereby contact the working electrode with the acceleration solution. The controller may further have instructions for removing the acceleration solution from the analysis chamber and rinsing the analysis chamber with a rinse solution prior to (c).

In various embodiments, the electroplating specification relates to a capability of the additives in the electroplating bath of interest to fully fill a feature on a substrate through a bottom-up mechanism in an acceptable time frame. As noted above, this timeframe may be about 1 hour or less for various features and plating conditions.

The instructions for determining in (d) may take various forms. In one embodiment, the instructions in (d) include instructions to compare a current density at a relevant time from the current density trace output from (c) to a threshold current density. Alternatively or in addition, the instructions in (d) may include instructions to compare a time at which the current density trace output from (c) reaches a threshold current density to a threshold time. In some cases, the instructions in (d) may include instructions to integrate the current density trace output from (c) between a first time and a second time to calculate a charge density, and comparing the charge density to a threshold charge density. Further, the instructions in (d) may include instructions for calculating a ratio between a potential from the first potential trace output at a first time in (a) to a potential from the second potential trace output at a second time in (c), and comparing the ratio to a threshold ratio. The calibration data may include one or more of the parameters selected from the group consisting of: a threshold current density, a threshold charge density, a threshold time, and a threshold ratio of potentials.

The apparatus may further include a counter electrode and a reference electrode. The counter electrode may be housed in a separated counter electrode chamber. The apparatus may further include a membrane separating the counter electrode from the working electrode. The membrane may form a part of the separated counter electrode chamber. The working electrode may take different forms. In some cases, the working electrode is a rotating disk electrode. In other cases, the analysis chamber is a flow-through cell. In this case, the apparatus may include a channel through which fluid may flow, and the electrode may be positioned in/on the channel.

In various embodiments, the inlet for providing test bath solution from an electroplating bath of interest to the analysis chamber is connected with an electroplating apparatus for electroplating metal onto semiconductor substrates using the electroplating bath of interest. The apparatus may further include a gas inlet for providing inert gas to the analysis chamber. The gas inlet may be a sparge tube in some cases, for example for providing nitrogen gas to de-oxygenate fluids in the electroplating bath of interest. In some cases, the analysis chamber may be configured to permit vacuum conditions within the analysis chamber. In these cases, the controller may further include instructions for applying vacuum conditions to the analysis chamber.

These and other features will be described below with reference to the associated drawings.

BRIEF DESCRIPTION OF THE DRAWINGS

FIGS. 9A-9C show experimental results comparing three different techniques in four different electrolyte test solutions.

DETAILED DESCRIPTION

Figure 1:
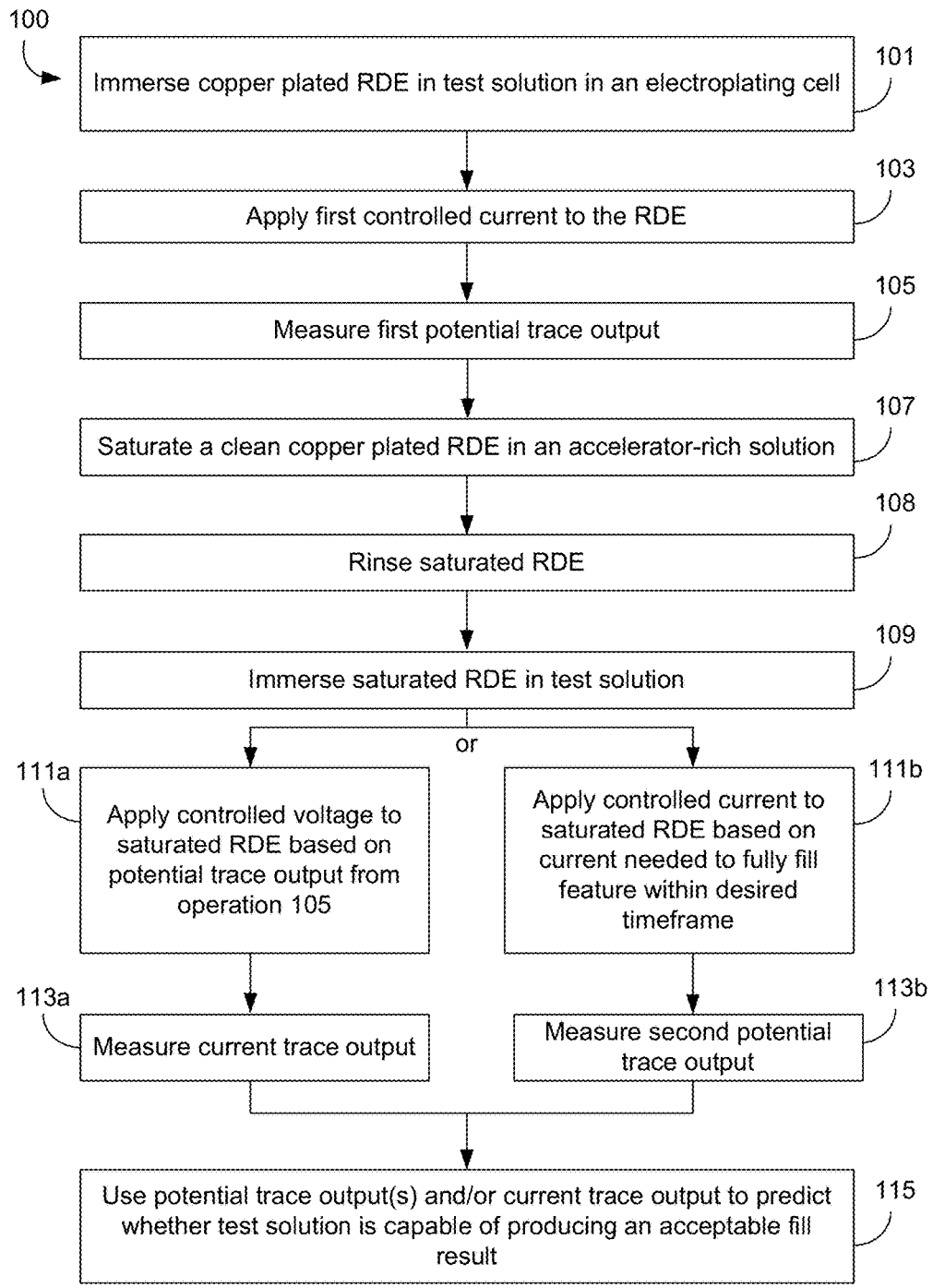
FIG. 1 is a flowchart depicting a method of predicting whether a bath will produce a successful bottom-up fill according to a disclosed embodiment.

In this application, the terms "semiconductor wafer," "wafer," "substrate," "wafer substrate," and "partially fabricated integrated circuit" are used interchangeably. One of ordinary skill in the art would understand that the term "partially fabricated integrated circuit" can refer to a silicon wafer during any of many stages of integrated circuit fabrication thereon. A wafer or substrate used in the semiconductor device industry typically has a diameter of 200 mm, or 300 mm, or 450 mm. Further, the terms "electrolyte," "plating bath," "bath," and "plating solution" are used interchangeably. The following detailed description assumes the invention is implemented on a wafer. However, the invention is not so limited. The work piece may be of various shapes, sizes, and materials. In addition to semiconductor wafers, other work pieces that may take advantage of this invention include various articles such as printed circuit boards and the like.

In the following description, numerous specific details are set forth in order to provide a thorough understanding of the presented embodiments. The disclosed embodiments may be practiced without some or all of these specific details. In other instances, well-known process operations have not been described in detail to not unnecessarily obscure the disclosed embodiments. While the disclosed embodiments will be described in conjunction with the specific embodiments, it will be understood that it is not intended to limit the disclosed embodiments.

While much of the discussion herein focuses on the use of copper plated electrodes and copper-containing plating solutions, it is understood that the embodiments are not so limited, and that the disclosed techniques may be used with a variety of plating metals such as nickel, tin, various alloys, etc. Further, although the discussion focuses on filling TSV features, the techniques may be used for predicting the fill of various recessed features.

Plating additives such as suppressors, accelerators and levelers are often used in electroplating processes to promote favorable fill mechanisms and results.

Suppressors

While not wishing to be bound to any theory or mechanism of action, it is believed that suppressors (either alone or in combination with other bath additives) are surface-kinetic polarizing compounds that lead to a significant increase in the voltage drop across the substrate-electrolyte interface, especially when present in combination with a surface chemisorbing halide (e.g., chloride or bromide). The halide may act as a chemisorbed-bridge between the suppressor molecules and the wafer surface. The suppressor both (1) increases the local polarization of the substrate surface at regions where the suppressor is present relative to regions where the suppressor is absent, and (2) increases the polarization of the substrate surface generally. The increased polarization (local and/or general) corresponds to increased resistivity/impedance and therefore slower plating at a particular applied potential.

It is believed that suppressors are not significantly incorporated into the deposited film, though they may slowly degrade by electrolysis or chemical decomposition in the bath over time. Suppressors are often relatively large molecules, and in many instances they are polymeric in nature (e.g., polyethylene oxide, polypropylene oxide, polyethylene glycol, polypropylene glycol, etc). Other examples of suppressors include polyethylene and polypropylene oxides with S- and/or N-containing functional groups, block polymers of polyethylene oxide and polypropylene oxides, etc. The suppressors can have linear chain structures or branch structures or both. It is common that suppressor molecules with various molecular weights co-exist in a commercial suppressor solution. Due in part to suppressors' large size, the diffusion of these compounds into a recessed feature can be relatively slow compared to other bath components.

Accelerators

While not wishing to be bound by any theory or mechanism of action, it is believed that accelerators (either alone or in combination with other bath additives) tend to locally reduce the polarization effect associated with the presence of suppressors, and thereby locally increase the electrodeposition rate. The reduced polarization effect is most pronounced in regions where the adsorbed accelerator is most concentrated (i.e., the polarization is reduced as a function of the local surface concentration of adsorbed accelerator). Example accelerators include, but are not limited to, dimercaptopropane sulfonic acid, dimercaptoethane sulfonic acid, mercaptopropane sulfonic acid, mercaptoethane sulfonic acid, bis-(3-sulfopropyl) disulfide (SPS), and their derivatives. Although the accelerator may become strongly adsorbed to the substrate surface and generally laterally-surface immobile as a result of the plating reactions, the accelerator is typically not significantly incorporated into the film. Thus, the accelerator remains on the surface as metal is deposited. As a recess is filled, the local accelerator concentration increases on the surface within the recess. Accelerators tend to be smaller molecules and exhibit faster diffusion into recessed features, as compared to suppressors.

Levelers

While not wishing to be bound by any theory or mechanism of action, it is believed that levelers (either alone or in combination with other bath additives) act as suppressing agents, in some cases to counteract the depolarization effect associated with accelerators, especially in exposed portions of a substrate, such as the field region of a wafer being processed, and at the side walls of a feature. The leveler may locally increase the polarization/surface resistance of the substrate, thereby slowing the local electrodeposition reaction in regions where the leveler is present. The local concentration of levelers is determined to some degree by mass transport. Therefore, levelers act principally on surface structures having geometries that protrude away from the surface. This action "smooths" the surface of the electrodeposited layer. It is believed that in many cases the leveler reacts or is consumed at the substrate surface at a rate that is at or near a diffusion limited rate, and therefore, a continuous supply of leveler is often beneficial in maintaining uniform plating conditions over time.

Leveler compounds are generally classified as levelers based on their electrochemical function and impact and do not require specific chemical structure or formulation. However, levelers often contain one or more nitrogen, amine, imide or imidazole, and may also contain sulfur functional groups. Certain levelers include one or more five and six member rings and/or conjugated organic compound derivatives. Nitrogen groups may form part of the ring structure. In amine-containing levelers, the amines may be primary, secondary or tertiary alkyl amines. Furthermore, the amine may be an aryl amine or a heterocyclic amine. Example amines include, but are not limited to, dialkylamines, trialkylamines, arylalkylamines, triazoles, imidazole, triazole, tetrazole, benzimidazole, benzotriazole, piperidine, morpholines, piperazine, pyridine, oxazole, benzoxazole, pyrimidine, quonoline, and isoquinoline. Imidazole and pyridine may be especially useful. Other examples of levelers include Janus Green B and Prussian blue. Leveler compounds may also include ethoxide groups. For example, the leveler may include a general backbone similar to that found in polyethylene glycol or polyethyelene oxide, with fragments of amine functionally inserted over the chain (e.g., Janus Green B). Example epoxides include, but are not limited to, epihalohydrins such as epichlorohydrin and epibromohydrin, and polyepoxide compounds. Polyepoxide compounds having two or more epoxide moieties joined together by an ether-containing linkage may be especially useful. Some leveler compounds are polymeric, while others are not. Example polymeric leveler compounds include, but are not limited to, polyethylenimine, polyamidoamines, and reaction products of an amine with various oxygen epoxides or sulfides. One example of a non-polymeric leveler is 6-mercapto-hexanol. Another example leveler is polyvinylpyrrolidone (PVP).

Bottom-Up Fill

In the bottom-up fill mechanism, a recessed feature on a plating surface tends to be plated with metal from the bottom to the top of the feature, and inward from the side walls towards the center of the feature. It is important to control the deposition rate within the feature and in the field region in order to achieve uniform filling and avoid incorporating voids into the features. The three types of additives described above are beneficial in accomplishing bottom-up fill, each working to selectively increase or decrease the polarization at the substrate surface.

After the substrate is immersed in electrolyte, the suppressor adsorbs onto the surface of the substrate, especially in exposed regions such as the field region. At the initial plating stages, there is a substantial differential in suppressor concentration between the top and bottom of a recessed feature. This differential is present due to the relatively large size of the suppressor molecule and its correspondingly slow transport properties. Over this same initial plating time, it is believed that accelerator accumulates at a low, substantially uniform concentration over the entire plating surface, including the bottom and side walls of the feature. Because the accelerator diffuses into features more rapidly than the suppressor, the initial ratio of accelerator:suppressor within the feature (especially at the feature bottom) is relatively high. The relatively high initial accelerator:suppressor ratio within the feature promotes rapid plating from the bottom of the feature upwards and from the sidewalls inwards. Meanwhile, the initial plating rate in the field region is relatively low due to the lower ratio of accelerator:suppressor. Thus, in the initial plating stages, plating occurs relatively faster within the feature and relatively slower in the field region.

As plating continues, the feature fills with metal and the surface area within the feature is reduced. Because of the decreasing surface area and the accelerator substantially remaining on the surface, the local surface concentration of accelerator within the feature increases as plating continues. This increased accelerator concentration within the feature helps maintain the differential plating rate beneficial for bottom-up fill.

In the later stages of plating, particularly as overburden deposits, the accelerator may undesirably build up in certain regions (e.g., above filled features), resulting in local faster-than-desired plating. Leveler may be used to counteract this effect. The surface concentration of leveler is greatest at exposed regions of a surface (i.e., not within recessed features) and where convection is greatest. It is believed that the leveler displaces accelerator, increases the local polarization and decreases the local plating rate at regions of the surface that would otherwise be plating at a rate greater than at other locations on the deposit. In other words, the leveler tends, at least in part, to reduce or remove the influence of an accelerating compound at the exposed regions of a surface, particularly at protruding structures. Without leveler, a feature may tend to overfill and produce a bump. Therefore, in the later stages of bottom-up fill plating, levelers are beneficial in producing a relatively flat deposit.

The use of suppressor, accelerator and leveler, in combination, may allow a feature to be filled without voids from the bottom-up and from the sidewalls-inward, while producing a relatively flat deposited surface. The exact identity/composition of the additive compounds are typically maintained as trade secrets by the additive suppliers, thus, information about the exact nature of these compounds is not publicly available.

Because the additive concentrations change over the course of plating, it is beneficial to have some sort of monitoring system in place to ensure that a particular plating bath will produce good bottom-up fill results. Otherwise, as the composition of the bath drifts over time, the bath will begin to produce sub-standard fills (e.g., incomplete fills) and may result in the loss of valuable, costly substrates.

One advantage of the disclosed techniques is that they enable holistic evaluation of the ability of a particular bath to fill a feature, rather than requiring individual determinations of the concentration of each additive/breakdown product. This is especially beneficial where the bath failure is being caused by the presence of an unknown/unrecognized material. Because the conventional methods are intended to evaluate the concentration of specific individual species, the presence of unrecognized problem causing materials will not be detected (as there will be no test specifically looking for the unrecognized material). The disclosed techniques therefore simplify the testing procedure and more accurately determine whether a bath will be successful.

This accurate determination is beneficial both in producing high quality products and in preventing loss of valuable substrates. Some types of fill failure, such as the incorporation of a void into a filled feature, are not able to be detected without destroying the substrate (e.g., by performing tests such as SEM/FIB, X-ray, ultrasound, interference microscopy, etc. to look inside the features on the substrate). As such, these failures may go undetected, and the void-containing feature may result in a sub-standard device. The disclosed techniques alert an operator when a bath is likely to fail/produce a void, such that remedial action can be taken to adjust or change the bath before it is used to process a substrate. In this way, the production of high quality products can be ensured. Further, at the point in production at which the recessed feature is being filled, the substrates have typically undergone a substantial amount of processing and are very valuable/expensive. By alerting an operator of sub-standard bath conditions before the bath is used to process the substrate, the loss of valuable substrates due to incomplete or otherwise unsuccessful fills can be avoided, resulting in considerable cost savings.

As used herein, a bottom-up fill process is considered successful if the feature is fully filled within a reasonable processing timeframe (e.g., about an hour), and is free of voids.

Methods

Certain embodiments herein relate to a method of determining whether a particular electroplating bath solution is able to produce acceptable bottom-up fill results using a set of two or more linked experiments, where the combined results of the experiments indicate whether the current plating bath (containing various concentrations of both desired additives and inorganic electrolyte components and undesired or unknown brake-down products or impurities) is likely to satisfy various necessary process conditions associated with a successful feature formation process, such as, but not limited to, sufficient field suppression, bottom-up filling initiation, bottom up filling rate, and final fill shutdown (reduction of acceleration and control of feature bump out size). For example, the combined results of the experiment can indicate whether the test bath is likely to succeed or fail at bottom-up filling a target feature. In a first embodiment, the first experiment is a current-controlled experiment and a second experiment is a potential-controlled experiment. In a second embodiment, both the first and second experiments are current-controlled experiments.

In each embodiment, the first experiment simulates the chemical and process conditions (e.g., surface and solution concentrations, flows, electric fields, and ion flux/currents) and voltage response experienced near wafer interface regions of the substrate that are non-recessed (e.g., the flat field region of the substrate) using a copper-plated electrode in the solution to be analyzed. The second experiment in each case is designed to simulate conditions (e.g., chemical state, polarization and current) present in a TSV feature of a substrate during electroplating, using a substantially fully accelerated copper-plated electrode in the solution to be analyzed.

In embodiments where the second experiment is potential-controlled, the potential applied during electroplating (whether static or dynamic) may be derived from the potential trace output of the first experiment (i.e., the potential experienced in the cell over time). In embodiments where the second experiment is current-controlled, the current density applied during electroplating (whether static or dynamic) may be chosen based on the current needed to fully fill the feature in an acceptable time frame (typically about 1 hour or less, as specific examples between about 5-40 minutes for 6×60 µm or 3×60 µm structures, and between about 10-60 minutes for 10×100 µm structures).

In the second experiment, the plated electrode surface is substantially fully accelerated prior to electroplating. The substantially fully accelerated surface may be produced through a pre-treatment that involves contacting the electrode with a concentrated accelerator-rich solution. A fully accelerated surface is one that cannot be further accelerated by further exposure to accelerator, whether by longer contact with an accelerator solution or contact with a higher concentration of accelerator. A substantially fully accelerated surface is a surface that has an accelerator concentration that functions in substantially the same manner as a surface of a recessed feature in a substrate. In some embodiments, a substantially fully accelerated surface has accelerator adsorbed at a level of at least about 80% of the concentration needed for a fully accelerated surface, for example at least about 90%.

In some cases, the accelerator-rich solution (also referred to as accelerator solution or acceleration solution) is held in an acceleration solution reservoir. The acceleration solution reservoir may be local to the metrology apparatus, or it may be positioned on an electroplating apparatus for electroplating material on substrates. For instance, the acceleration solution may be delivered from an additive reservoir that is used to periodically dose electrolyte used in electroplating on substrates.

Another way to describe the substantially fully accelerated surface is the fractional acceleration (f) of the surface, which is a measure of the relative amount of accelerated deposition (related to the depolarization for electroplating). The fractional acceleration is typically between about 0-1, and it is a relative measure of degree of acceleration. In particular, a fractional acceleration value of 0 corresponds to a surface that does not have any accelerator (slowest deposition), while a fractional acceleration value of 1 corresponds to a surface that is fully saturated with accelerator (fastest deposition) and any further exposure to accelerator (through higher concentration accelerator solutions or longer exposure time) does not produce faster deposition. The fractional acceleration can be a function of many parameters, but for this discussion is related to the amount of accelerator (surface concentration or accelerator dosing exposure duration) on the surface. Because the electrode is flat/featureless, the surface concentration should be fairly uniform. The fractional acceleration can be measured for a particular set of operating conditions by the following relationship:

$$f=(I_{acc}-I)(I_{acc}-I_{sup})$$

where:
f=the fractional acceleration of the surface,
Iacc=the metal deposition current density (or deposition rate) with a saturated surface concentration of adsorbed accelerator,
Isup=the current density (or deposition rate) on a surface deposited under the exact same conditions except with no adsorbed accelerator, and
I=is the current density (or deposition rate) on the surface being evaluated In certain embodiments, the fractional acceleration of the surface when it is substantially fully accelerated is at least about 0.8, or at least about 0.9, or at least about 0.95.

The experiments may take place in an electrochemical cell that is used primarily for analyzing electrolyte such as, for example, the QLC series of automated chemical monitoring systems available from ECI Technology of Totowa, N.J., or an ancolyzer system from Ancosys of Pliezhausen, Germany. The experiments may also be done in an electrochemical cell of an electroplating apparatus that is primarily used for other processes, e.g., filling TSVs. However, due to the relatively long time frame of the experiments (e.g., 1+ hours), and the need to modify the plating chamber (e.g., the addition of a reference electrode), it is generally preferable to perform the tests in a separate cell used primarily for analysis. Where a separate cell is used, a sample of the solution to be tested should be introduced into the cell to serve as the electrolyte during the experiments. The analysis can be conducted while electroplating in the principal electroplating cell. An appropriate electrochemical metrology tool is discussed below in relation to FIGS. 2A and 2B, and multi-station processing tools incorporating a metrology tool are discussed below in relation to FIGS. 3 and 4. With the combined results from the two experiments, accurate predictions can be made regarding whether a particular bath will produce acceptable bottom-up fill results. These experiments and predictions may be referred to as the Bath Filling Pass Fail quality tests (BFPF tests).

The disclosed techniques are especially useful in the TSV filling context, though they are not so limited. The techniques may be applied to evaluate the ability of a variety of plating baths to fill various types of recessed features. In some cases, the bath being evaluated is used to fill recessed features that are greater than about 1 micron wide. The recessed feature may also be less than about 20 microns wide. In these or other cases, the recessed features have an aspect ratio that is greater than about 5:1. The recessed features may also have an aspect ratio that is less than about 50:1. Another reason that the disclosed techniques are especially useful for TSV filling is that this type of process occurs over a relatively long time frame (e.g., greater than about 10 minutes, or greater than about 30 minutes). Certain bath components may break down over these long time frames, causing particular modes of fill failure that do not generally arise in shorter timeframe contexts (e.g., damascene filling). The disclosed techniques may be used to detect these long time frame effects.

First Experiment

As mentioned above, the first experiment is a current-controlled experiment performed to simulate the conditions experienced near the field of a substrate. The first experiment may be performed in a galvanostatic mode or in a galvanodynamic mode. Among other things, this experiment by itself allows one to compare the field suppression value (the field overvoltage) from a known good bath vs. the field suppression of the current unknown-state bath. It also establishes a value for the applied potential response for the target current waveform (current over time) process in the unknown bath, and can be applied in subsequent experiments to illuminate more relevant information, discussed further below. Also, this experiment can be used to certify that the field suppression is maintained at a sufficient and/or stable level throughout the entire time domain of the feature filling process (e.g., if the field starts suppressed, but subsequently loses suppression, the filling process may start slowly and stop late in the operation).

FIG. 1 provides a flowchart for performing a method in accordance with various embodiments herein, and provides details relating to both the first and second experiments. The process 100 starts at block 101 where a pre-plated electrode (e.g., an RDE pre-plated with copper, though other electrodes and other plating materials may be used) is immersed in a test solution in an electrochemical cell The RDE is typically made of platinum, and should be pre-plated in an electrolyte that is free of additives (i.e., in electrolyte which is substantially void of species which would cause an impure copper deposit, or which would alter/inhibit the activity/polarization of the electrode surface by leaving surface adsorbed species that would modify the charge transfer for a copper deposition process, e.g., electrolyte which is free of levelers). In some embodiments the solution for pre-plating the electrode is a virgin makeup solution (VMS).

In various cases, the RDE is typically plated with substantially pure copper. However, in cases where the plating solution in question is used to plate a metal other than copper, the RDE may be plated with this other metal. In either case, the metal plating should be substantially free of species that would alter the activity/polarization of the electrode surface. The thickness of the pre-plating may be more than about 250 Å, and may also be less than about 2 µm. The test solution is the electroplating solution that is being evaluated (i.e., the solution with an unknown bottom-up filling characteristic/ability).

In various embodiments, the electrochemical cell has a total of three electrodes. The first electrode is the copper plated RDE, which acts as a cathode/working electrode. The working electrode is tied to the potentiostat as the electrochemical response (e.g., potential or current) is measured. The second electrode is the counter electrode (e.g., an inert anode or a metal electrode such as a copper electrode), which may be separated from the copper plated RDE. In one embodiment the counter electrode is separated from the RDE by a membrane (e.g., a cationic membrane, an anionic membrane or a microporous membrane). The use of a membrane can help prevent formation and interference of by-products created at the anode through oxidation, for example oxidation of organic plating additives. These by-products may interfere with the activity of the working electrode and the data signal.

In another embodiment, the counter electrode is housed in a first container while the RDE and test solution are housed in a second container, where the two containers are connected via a salt bridge. In a third embodiment, the counter electrode is immersed in the test solution and is not separated from the RDE. Where the counter electrode is separated from the test solution, the solution in which the counter electrode is immersed may be the same as, similar to, or different from the test solution exposed to the working electrode. The third electrode is a reference electrode, which provides a reference potential for comparison to the potential of the working electrode. The reference electrode is used to accurately collect a reliable set of data in each experiment. Suitable reference electrodes may be any of those conventionally used, including, but not limited to, $Hg/HgSO_4$ or $Ag/AgCl$.

At block 103, a first controlled current/current density is applied to the electrode. The first experiment may be performed under conditions representative of the plating process for which the test solution is being used. These representative conditions include the waveform or open-area corrected waveform (current density as a function of time, which may be galvanostatic or galvanodynamic), temperature, rotation rate of the RDE, deoxygenation/degassing procedures, etc. For example, where the process for filling the recessed feature on a wafer substrate is performed at a constant applied current density, for example at about 2 $mA/cm^2$, the first current-controlled experiment may also be performed at a constant applied current density of 2 $mA/cm^2$. Similarly, where the process for filling the recessed feature on the substrate is performed with a dynamic current-controlled waveform (e.g., with steps, ramps, pulses, periods of constant current, or a combination of these elements), the first current-controlled experiment may be performed with a substantially identical dynamic waveform.

A goal is to use an appropriate first controlled current that is representative of the current density applied to the field region of the wafer. The current density may be equal to or nearly equal to the current density of the full wafer plating process, particularly for processes where the amount of via plating area is sufficiently low. For example, if the estimated charge used in filling the features is a relatively small fraction of the total charge (for example less than about 20%), then no correction may be necessary, and the current density waveform (current density over time) used to process the entire wafer may be used for this first experiment. This current density waveform may be appropriate because the field current density is approximately equal to the applied current density.

On the other hand, if the amount of charge in the features is greater than about 20 percent of the total charge delivered, then a substantial amount of current is going to filling the features (i.e., the field current density is notably less than the applied current density), and a corrected current density waveform may be suitable for this experiment. For example, one can estimate an appropriate field current density correction factor to the full-wafer waveform based on the plating metal field thickness on wafers that are known to be plated acceptably. For example, the field current density correction factor may be calculated by comparing the amount of charge needed to plate metal to the desired thickness in the field region, and the total amount of charge delivered during electroplating. Alternatively, the field current density correction factor can be estimated based on the amount of metal plated in the vias (or other recessed structures). In this case, the correction factor may be calculated by comparing the amount of charge needed to fill the sum-total of all the vias to the total charge passed in the deposition process.

The field current density correction factor represents the fraction of the total charge delivered during electroplating which is used to deposit metal in the field region (as opposed to charge used to deposit metal in the features, for example). The field current density correction factor may be used to calculate an appropriate current density to apply during the first experiment. In one example, about 40% of the total charge delivered during a relevant full-wafer electroplating process is used to deposit metal in the features, and about 60% of the total charge is used to deposit in the field region. The field current density correction factor in this case is about 0.6. Therefore, the current density applied during the first experiment may be about 0.6 times the current density applied during the full-wafer process. This analysis applies for both galvanostatic and galvanodynamic waveforms. For instance, where a galvanodynamic waveform is used to plate on the full wafer, a similar galvanodynamic waveform (differing only in the magnitude of applied current) may be used in the first experiment.

In some cases, the conditions used during the first experiment depart from the conditions used during electroplating on substrates. One reason for departing from the actual plating conditions is to perform the experiments in a shorter timeframe. For example, the rotation rate of the RDE and/or the temperature of the electrolyte may be higher during the first current-controlled experiment than during plating on substrates. These changes allow for a faster determination of a final potential reached by the electrolyte. One of ordinary skill in the art is able to choose conditions that appropriately match the plating conditions, and therefore, these conditions will not be described in detail.

It would be recognized by one of ordinary skill in the art that current and current density are closely related. The current density is simply a measure of the current provided to the electrode per surface area of the electrode. As such, applying a controlled current is equivalent to applying a controlled current density, and measuring a current trace output is equivalent to measuring a current density trace output.

At block 105, the potential trace output of the system (potential vs. time response to the first imposed current-controlled waveform) is measured and recorded. The potential trace output from this experiment may be used to determine the applied potential at which the second experiment should be performed, in certain implementations. In some embodiments, the potential trace output of the first experiment is used directly in a final technique for determining whether the bath will produce an acceptable fill. The remaining operations shown in FIG. 1 will be discussed in the next sections.

Second Experiment

The second experiment may be a potential-controlled or current-controlled procedure designed to simulate the conditions present in a feature (e.g., the bottom of a TSV feature being filled) of a plating substrate. In other words, this experiment may be considered to be a "feature filling simulation." Among other things, one objective of this experiment is to project whether or not the bath in question can support a sufficiently high within-feature deposition rate to complete the filling process in the target process allotted time. A within-feature surface is simulated as a highly accelerated surface. In some embodiments, the deposition rate of the highly accelerated surface at the potential established in the first experiment gives an indication of the maximum deposition rate and relative field to feature filling rates (i.e., contrast). As such, the deposition rate and field to feature filling rate contrast observed in the experiments can be compared to previously established baselines to indicate the likelihood of a bath related issue and filling failure. The baselines may be established based on experimental testing of baths that are known to produce good and bad fill results, discussed further below.

The second experiment may be performed on the same electrode that was used in the first experiment, or it may be performed on a different electrode. Where the same electrode is used, it should be adequately cleaned before use to remove the copper (or other metal) plating. In one embodiment, the cleaning process involves electrochemical anodization. In this case, a positive potential or an anodic current is applied to the electrode in order to dissolve the metal plated on the electrode surface. In another embodiment, the cleaning process involves etching the surface with a copper (or other metal) etchant (e.g., solutions of hydrogen peroxide/sulfuric acid, ammonium persulfate, ferric chloride, or concentrated nitric acid (>15%)). After the metal is removed from the surface of the electrode, it is completely rinsed before being pre-plated with metal for the second experiment. For the sake of clarity, the remaining description will focus on embodiments where the plating solution is used for plating copper and the RDE is therefore plated with copper. However, one of ordinary skill in the art would understand that any of various electroplating solutions/metals may be used.

Returning to FIG. 1, at block 107 a clean copper plated RDE is pre-treated through a chemical or electrochemical method by contacting it with a chemisorbing accelerator-rich solution in order to substantially completely saturate the surface with accelerator. This saturation closely approximates the surface conditions present in a TSV feature being filled because, as explained above in the Bottom-Up Fill section, accelerator accumulates inside the features (especially on the surfaces of the features) as they are filled. The solution used for pre-treating the RDE should contain concentrated, relatively strong accelerator (as compared to the test solution). The pre-treatment process for saturating the surface of the electrode is further discussed and described in the following U.S. Patent documents: U.S. patent application Ser. No. 13/711,254, filed Dec. 11, 2012, and titled "MONITORING LEVELER CONCENTRATIONS IN ELECTROPLATING SOLUTIONS"; U.S. Provisional Patent Application No. 60/724,209, filed Oct. 5, 2005, and titled "SELECTIVE ELECTROCHEMICAL ACCELERATOR REMOVAL"; U.S. Pat. No. 7,405,163, filed on Apr. 13, 2004, and titled "SELECTIVELY ACCELERATED PLATING OF METAL FEATURES"; U.S. Pat. No. 7,449,098, filed on Dec. 17, 2003, and titled "METHOD FOR PLANAR ELECTROPLATING"; U.S. Pat. No. 7,449,099, filed on Sep. 21, 2004, and titled "SELECTIVELY ACCELERATED PLATING OF METAL FEATURES"; U.S. Pat. No. 7,531,079, filed on Feb. 23, 2005, and titled "METHOD AND APPARATUS FOR UNIFORM ELECTROPOLISHING OF DAMASCENE IC STRUCTURES BY SELECTIVE AGITATION"; U.S. Pat. No. 7,560,016, filed on Nov. 7, 2008, and titled "SELECTIVELY ACCELERATED PLATING OF METAL FEATURES"; U.S. Pat. No. 7,799,200, filed on Oct. 5, 2006, and titled "SELECTIVE ELECTROCHEMICAL ACCELERATOR REMOVAL"; and U.S. Pat. No. 8,268,154, filed on Aug. 20, 2010, and titled "SELECTIVE ELECTROCHEMICAL ACCELERATOR REMOVAL," each of which is herein incorporated by reference in its entirety.

In some cases, the pre-treatment includes contacting an already pre-plated adsorbate-free RDE with an accelerator-rich solution (e.g., a solution having accelerating thiol species such as a solution of mercaptopropane sulfonic acid (MPS) and/or dimercaptopropane sulfonic acid (SPS), also referred to as acceleration solution or accelerator solution) for a time period sufficient to substantially completely saturate the surface with accelerator. Pre-plating the electrode may occur as described above, in a solution that is free of species that could interfere with subsequent accelerations (e.g., solution free of leveler). Contact of a pre-plated electrode with an accelerator-rich solution involves chemical activation of the electrode surface. In a particular embodiment, the acceleration solution for chemically accelerating the electrode surface contains MPS. The acceleration solution may be free of species that could interfere with the electrochemical activation of the copper surface, e.g., levelers. The contact may occur through, for example, dipping, spraying, etc.

In other cases, the pre-plating and pre-treatment are combined into a single step where the RDE is pre-plated with copper in an accelerator-rich solution. In this case, the electrode surface is activated through an electrochemical process. In these embodiments, the activation of the electrode surface is accomplished by a simultaneous electrochemical reduction of SPS and the deposition of copper. In one example, the acceleration solution used for electrochemically activating the surface with accelerator includes SPS, copper ions, acid, and optionally a suppressor. MPS may also be used in place of (or in addition to) SPS. The acceleration solution may be free of any species that could interfere with the electrochemical activation of the copper surface. For instance, the acceleration solution may be free of leveler, as noted above. The acceleration solution may optionally include a suppressor additive in some embodiments. In other cases, the acceleration solution may be substantially free of any organic additives other than accelerators.

In some embodiments, the accelerator-rich solution has an accelerator concentration that is at least about 10 times, or at least about 50 times, or at least about 100 times as high as that in the test solution.

An adsorbate-free copper pre-plated electrode may be prepared by plating a platinum electrode in a copper electrolyte containing e.g., minerals or alkyl acids (e.g., sulfuric acid, methanesulphonic acid), low concentration of chloride ions (e.g., about 50 ppm), and/or any copper non-chemically bonding and specifically adsorbing set of materials, such as the PEO/PEG class suppressor molecule. The PEO/PEG suppressor molecules do not interfere with the results because they do not permanently adsorb onto the electrode, and their presence in the electrolyte does not alter the electrochemical activity of the plated copper or the copper interface.

The time period for achieving substantially complete activation/saturation of the surface will depend on several factors including the accelerator concentration in the pre-treatment solution, the convective conditions present, temperature, potential, etc. Generally, the use of longer timeframes helps ensure complete or substantially complete saturation/activation of the surface. Separate standardizing tests may be performed to determine the time required to fully activate the surface. In one example the standardizing tests involve exposing electrodes to an appropriate accelerator-rich solution for different time periods to determine the time beyond which additional exposure does not lead to a further decrease in electrode depolarization in a solution, e.g., a solution containing copper, acid, chloride, and a PEG/PEO class suppressor. In a particular example, a pre-plated RDE is fully activated by exposing the plated RDE to a solution of SPS or MPS having a concentration of at least about 0.01 mol/L, at a temperature of at least about 20° C., rotating at a speed of at least about 100 RPM, for a time period of at least about 15 seconds. Full acceleration (also referred to as full activation) may be accomplished at shorter or longer time frames using higher/lower accelerator concentrations, higher/lower temperatures, and/or higher/lower convection conditions, etc. The choice of accelerator can also affect the timeframe needed for activating the surface. For example, MPS may activate the surface somewhat more quickly than SPS. However, the depolarization achieved at saturated activation conditions has shown to be essentially identical between these two cases.

In some embodiments, the pre-treatment solution may be free of any strongly chemisorbing or electrochemically activated chemisorbing surface active species that could bond to and interfere with the adsorption of the accelerator compound to the copper surface. This may help produce a surface that is appropriately saturated with accelerator. One group of materials that may be excluded from the pre-treatment solution in various embodiments is the class of materials known as levelers, which are further described above. Materials that adsorb and interfere in creating a substantially saturated surface concentration of accelerator adsorbate, or that would otherwise increase the polarization of the surface relative to a fully accelerator-activated surface may be avoided.

As with the copper plated RDE used for the first experiment, the thickness of the pre-plating may be more than about 250 Å, and may also be less than about 2 μm. This pre-treatment process may also be referred to as an "activation" process.

After activating the surface with accelerator, the surface should be rinsed (e.g., with water) at block 108. This rinsing procedure removes remnants of the strongly activating pre-treatment solution, and prevents the transfer of pre-treatment solution (and species therein) to the test solution. Accelerator species that are chemisorbed to the surface of the RDE will substantially remain attached to the plated/activated RDE surface, both during rinsing and during the second experiment.

Next, at block 109 the saturated RDE is immersed in test solution in an electrochemical cell. The electrochemical cell used in the first and second experiments may be the same or different. Like the electrochemical cell used in the first experiment, the electrochemical cell used in the second experiment may have about three electrodes (a working RDE electrode, a counter electrode and a reference electrode), and the electrolyte present in the electrochemical cell is the test solution. The saturated RDE may be separated from the counter electrode, for example by a membrane or salt bridge.

Next, a controlled potential or controlled current may be applied to the saturated RDE. These are alternative options depicted as blocks 111a and 111b. The potential waveform (potential over time) or current density waveform (current density over time) may be designed to approximate the plating conditions (e.g., current, potential) experienced within a feature on a substrate. At block 111a, a potentiostatic or potentiodynamic voltage may be applied to the saturated RDE. The voltage applied corresponds to a voltage output of the first experiment. In one embodiment, the voltage applied in the second experiment is the static, average potential during a final period in the potential trace output of the first experiment. The final period may cover the last about 5-15 minutes of the first experiment. In one implementation, the final period is about the last 10 minutes of the first experiment. In another embodiment, the voltage applied in the second experiment is a dynamic, linearly progressed potential designed to fit a final period in the potential trace output of the first experiment. In other words, the potential trace output of the first experiment, especially the output during a final period in the experiment, may be used to predict/extrapolate what the voltage of the system is likely to be over a subsequent period, and in some embodiments the voltage applied in the second experiment matches the prediction made based on the first experiment. Continuing this embodiment at block 113a, the current trace output of the second experiment is measured and recorded.

In an alternative embodiment where the second experiment is a current-controlled experiment as shown in block 111b, the current applied during the second experiment may be selected based on the current needed to fully fill the features within an acceptable timeframe (e.g., less than about 1 hour in some cases, though alternative timeframes are provided above). The current profile/waveform may be galvanostatic or galvanodynamic. Where the current profile is galvanostatic, the applied current may be selected/calculated based on the dimensions of the features and the empirically determined acceptable fill time. Where the current profile is galvanodynamic, the applied current/current density may be calculated based on the current density expected at the plating front of a feature during a final period of electroplating. The final period of electroplating may be the final 5-10 minutes, for example the final 10 minutes of an electroplating process, depending on the feature. This expected current density vs. time may be applied galvanodynamically in the second experiment. In either case, the current and current density calculations are based on a simple application of Faraday's law, as is familiar to those of ordinary skill in the art.

This embodiment continues at block 113b where the potential trace output of the second experiment is measured and recorded. This output is sometimes referred to as the second potential trace output.

In various embodiments, the current trace output or the second potential trace output is used in a technique to determine whether the bath will produce an adequate fill result. The second experiment runs for a time period sufficient to observe the eventual shape/trend of the current/potential trace output. In some cases, the second experiment runs for a period between about 5-15 minutes. In a particular example, the second experiment runs for a period of about 10 minutes. The temperature and rotation rate of the RDE may be the same as during the first experiment or may differ, for example to evaluate certain mass transport effects. It may be beneficial to use a higher rate of rotation and/or a higher temperature during the second experiment (as compared to the conditions used in the target filling process) to encourage any species which tend to break down or adsorb during the filling process to break down or adsorb more quickly, and to amplify the signal. In this way, the bath evaluation method may occur over a shorter period of time than would otherwise be required. While it may be possible to vary both the temperature and the rotation rate for the second experiment, it may be difficult to correctly interpret the electrochemical responses. As such, in some embodiments, either the temperature or the rotation rate is changed for the second experiment (relative to normal filling conditions), but not both.

At block 115, the results from the first and/or second experiment are used to determine whether the test solution is able to produce an acceptable fill result, as discussed in the following section.

Ideally during plating, the field region of a substrate will be highly suppressed (resulting in little film growth, and a highly polarized surface) over the entire time of the plating process. Further, the region inside a feature should ideally be highly accelerated, with low polarization and a high rate of fill, and current delivery that does not diminish too rapidly over time. The techniques disclosed in the following section take these concepts into account.

During the later stages of successful feature fill, the relative metal deposition rate inside the feature is much higher (typically 10× or greater) than the deposition rate in the field region. When the feature is nearly filled, it is typically desirable to have the relative deposition rate inside the feature become slower, the polarization of the surface as a whole increase, and the rate of deposition in the field increase. This process is called feature growth shutdown. This shutdown is desired to avoid excess feature fill/overplating, which can lead to the formation of an excess feature bump out overshoot. This excess feature bump, if present, can create processing difficulties and issues in upstream processing (e.g., during chemical mechanical polishing (CMP) removal of excessively high bumps).

While not wishing to be held to any particular model or theory, it is believed that in many cases the emerging feature growth "shutdown" is governed by the acceleration deactivating activity of a leveling compound. Monitoring of ultra-low activities/concentrations of leveling compound is further discussed in U.S. patent application Ser. No. 13/711,254 filed Dec. 11, 2012, titled, "MONITORING LEVELER CONCENTRATIONS IN ELECTROPLATING SOLUTIONS," and naming Steven T. Mayer as an inventor. The Ser. No. 13/711,254 application is incorporated by reference in its entirety. To better understand the functioning of the shutdown mechanism in a bath of interest, an additional or related experiment may be performed, as discussed in the Ser. No. 13/711,254 application. This experiment may specifically seek to characterize the performance of the leveler in the bath of interest. The experiment may involve pre-accelerating an electrode until it is substantially fully accelerated, plating the electrode in the bath of interest, and recording the electrochemical response of the electrode. The experiment may involve analyzing changes in the electrochemical response (e.g., current transient) over time and as a function of rotation rate of the pre-activated surface, and comparing the response to data generated from electroplating baths that are known to exhibit successful and unsuccessful fill behavior. The reason for a bath's poor performance may be related to a missing or insufficient concentration of a leveling compound, or an additional compound or compounds which are interfering with diffusion of the leveler, which impacts the suppressing/deactivating activity of the leveler. But whatever the cause, the analysis will allow one to confirm that accelerator-shutdown is or is not occurring as required to obtain the target desired results. Because leveler-based shutdown is typically diffusion controlled, it is a convection-dependent (e.g., rotation rate-dependent) parameter. As such, the convective conditions may be modulated during the second experiment to help probe the unknown bath's shutdown operation, in certain cases.

Determination of Whether a Plating Solution is Acceptable

The output of the two experiments may be used to predict whether the test solution will produce acceptable bottom-up fill results. An unacceptable fill result is one in which the fill is incomplete after a specified target filling time, or a fill that contains voids. For example, to be successful, a 60 μm deep feature that fills completely in "good" electrolyte should have an average predicted deposition rate in excess of about 1 μm/min. As a further example, to avoid the formation of voids, the ratio of current in the field region to that in the feature should not fall too low.

A number of different techniques/comparisons may be used to make the prediction. Various techniques are intended to provide a way to compare the plating rate in a field region vs. plating in a feature (for example, by calculating a ratio of the current densities). The ratio of the current density inside the feature to that on the field region is referred to as the plating contrast ratio. This ratio gives a measure of the ability of the bath to completely fill a feature. Because the current densities may change over time as the metal on the field or in the feature becomes more or less polarized due to changing electrochemical surface and electrolyte conditions, the plating contrast ratio may similarly change over time. A key factor in determining whether a bath will result in a successful bottom-up fill is whether the contrast ratio is maintained at a sufficiently high value for a sufficiently long period of time necessary for completion of the filling process. The filling time for a particular process will depend on factors such as the depth of the feature and the active feature current density or plating deposition rate.

At long times, most or all bad/unsuccessful baths exhibit lower potentials (i.e., they become less polarized) relative to the good/successful baths. This difference implies that the polarization at the surface is decreasing with time and is lower than that in a good bath, and that the applied potential within a feature will be lower for a bad bath than a good one at a point late in the filling process.

The following techniques present methods of determining (in a yes/no manner), whether the test bath is likely to produce a successful feature fill based on the output of the first and/or second experiments.

A few techniques for interpreting the experimental results will be provided, though one of ordinary skill in the art would understand that the experiments disclosed herein may be used to predict whether a plating solution will produce acceptable fill results by various different analysis techniques. In the disclosed techniques, the following notations will be used:

$t_1$=time $t_1$ during the first experiment,
$t_{2a}$=time $t_{2a}$ during the second experiment, where the second experiment is a potential-controlled experiment
$t_{2b}$=time $t_{2b}$ during the second experiment, where the second experiment is a current-controlled experiment
$Ex_1(t_1)$=the output voltage of the first experiment at time $t_1$,
$Ex_{2a}(t_{2a})$=the output current density of the second experiment at time $t_{2a}$, where the second experiment is a potential-controlled experiment,
$Ex_{2b}(t_{2b})$=the output voltage of the second experiment at time $t_{2b}$, where the second experiment is a current-controlled experiment,
$CD_{th}$=a threshold current density,
$t_{th}$=a threshold time,
$C_{th}$=a threshold amount of charge/area, referred to as the threshold charge density, and
$R_{th}$=a threshold ratio.

The first three techniques relate to an embodiment where the second experiment is a potential-controlled experiment. The fourth technique relates to an embodiment where the second experiment is a current-controlled experiment. The first technique compares the current density output of the second experiment at time ($t_1$) to a current density threshold ($CD_{th}$).

Technique 1:

The first technique compares the current density output of the second experiment at time ($t_1$) to a current density threshold ($CD_{th}$).

Fill will be successful if $|Ex_{2a}(t_{2a})|>CD_{th}$

The current density threshold ($CD_{th}$) and the relevant time ($t_{2a}$) are determined empirically based on baths that are known to produce acceptable and unacceptable fill results. This technique focuses on the concept that if the magnitude of the current density output is lower than the threshold value at a particular time, a region in the TSV feature will likely be insufficiently accelerated relative to the field region, and a resulting fill is likely to be incomplete or otherwise unsuccessful. Similarly, this technique addresses the idea that where the current density at time $t_1$ is too low, the feature is not expected to complete its filling in the standard filling time of the target process.

Technique 2:

A second technique compares the time (t) at which the current density output of the second experiment crosses a threshold current density ($CD_{th}$).

Fill will be successful if $|Ex_{2a}(t)|>CD_{th} \forall t<t_{th}$

The threshold current density ($CD_{th}$) and threshold time ($t_{th}$) are determined empirically based on baths that are known to produce acceptable and unacceptable fill results. This technique focuses on the concept that the fully accelerated surface used in the second experiment will experience a decrease in the magnitude of current density (e.g., current density becomes less negative) over time when exposed to a bath, and that if it takes too short a time to reach the threshold current density, the feature will not be fully filled before the filling process terminates. As such, the technique predicts that a fill will be successful if the absolute value of the output of the second experiment is greater than a threshold current density ($CD_{th}$) for all times before the threshold time (e.g., for all $t<t_{th}$). In other words, the time at which the output of the second experiment crosses the relevant current density threshold must be later than the threshold time in order to predict success.

Technique 3:

A third technique compares the integrated current density output from the second experiment over a time period between $t_{2a1}$ and $t_{2a2}$ to a threshold value of charge/area.

Fill will be successful if $|\int_{t_{2a1}}^{t_{2a2}} Ex2a(t)\, dt|>C_{th}$

Like the other threshold values used in Techniques 1 and 2, the threshold charge density ($C_{th}$) is determined empirically based on baths that are known to produce acceptable and unacceptable fill results. Likewise, the bounds on the time period over which the data is evaluated ($t_{2a1}$-$t_{2a2}$) are determined empirically. This technique focuses on the idea that if the amount of charge passed over a set period during the second experiment is too low, the acceleration effects will be lost too quickly and the feature will not fill completely.

Technique 4:

A fourth technique may be used in cases where both the first and second experiments are current-controlled. In this technique, a ratio between the voltage output of the first and second experiments is compared to a threshold ratio ($R_{th}$).

Fill will be successful if $Ex_1(t_1)/Ex_{2b}(t_{2b}) > R_{th}$

The threshold ratio may be determined empirically much like the other threshold values. This analysis technique focuses on the concept that if the polarization of the field region (indicated by the voltage output of the first experiment) is sufficiently high compared to the polarization of the feature region (indicated by the voltage output of the second experiment) at a relevant time (or times), then the plating contrast ratio will be sufficiently maintained, and the fill will proceed to completion.

Many of the disclosed techniques evaluate the data at particular times. As mentioned, these times are often determined empirically. The times are chosen by identifying and selecting times/timeframes with a relatively high contrast between a signal generated from a "good" bath and a signal generated from a "bad" bath (as compared to the other potential times/timeframes during plating).

Apparatus

The methods described herein may be performed by any suitable electroplating apparatus capable of monitoring potential and current density. A suitable apparatus may include hardware for accomplishing the process operations and a system controller having instructions for controlling process operations in accordance with the present invention. In some embodiments, the hardware may include one or more process stations included in a process tool.

As described above, the first and second experiments may be performed in an electrochemical cell that is used primarily for electroplating (e.g., filling TSVs), or in a separate electrochemical cell that is used primarily for testing solutions. In some cases, the electrochemical cell is a simple benchtop apparatus (e.g., a benchtop apparatus permitting temperature tuning, degassing, and circulation of a sample solution).

Figure 2A:
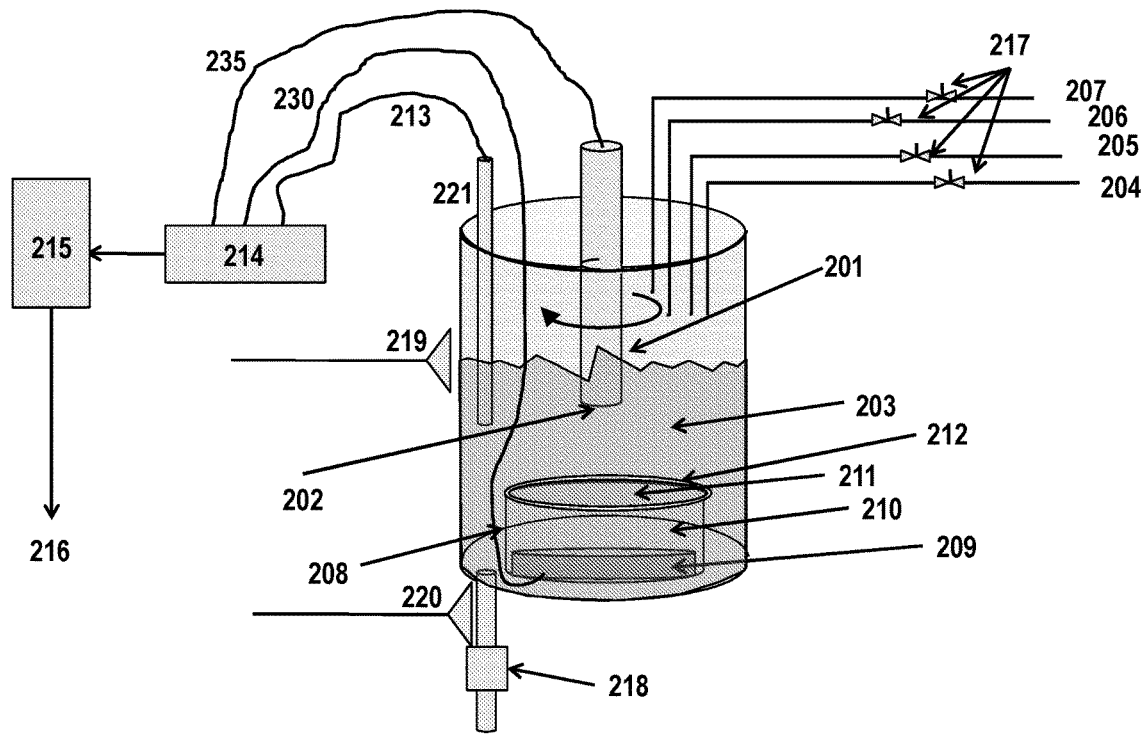
FIG. 2A shows a metrology tool according to a disclosed embodiment.

FIG. 2A shows an example of an electrochemical cell/metrology tool 200 according to a disclosed embodiment. In this example, the working electrode 201 for performing the electrochemical measurement is a rotating disk electrode composed of an outer cylindrical insulating material (e.g., plastic) surrounding a wire or rod for carrying current to the rotating disk surface 202. The disk surface 202 is often made of a noble metal such as platinum or gold. The various process fluids 203 used in the process (e.g., test solution, rinsing solution, activating solution, and etching solution) are delivered by separate lines 204, 205, 206, 207, supplied by a pressurized and valve (217) controlled delivery, or by a set of syringe pumps (not shown). The level of processing fluid 203 in the container can be controlled by level sensing devices 219 and 220. Level sensing device 219 senses the fluid level in the metrology tool 200 to ensure that the tool sufficiently fills with fluid as needed, while level sensing device 220 operates to detect that the fluid in the tool is sufficiently drained as needed.

The anode (also referred to as a counter electrode) 209 may be contained in a separate sealed container (also referred to as the anode compartment or counter electrode compartment) 208 with a bottom, side walls and a membrane 211 (e.g. a cationic membrane such as Nafion®, or an anionic membrane, or a microporous membrane) which keep the anode electrolyte solution 210 in the anode compartment 208. In this way, the anode electrolyte solution and the processing fluid (e.g., test solution) are fluidically separated from one another both during plating and during the rinsing and draining of the various liquids. This separation is beneficial for several reasons. For example, it is often desirable to maintain the anode electrolyte solution free of additives that may be present in the processing fluid. This helps prevent the reaction and degradation of the additives at the anode, which is at an anodic potential compared to the cathode RDE. Further, the separation is beneficial in preventing the formation and transport of potentially harmful cuprous ions at the anode. In some embodiments, the electrolyte present in the anode compartment 208 includes the same components as the electrolyte in contact with the working electrode, minus any organic plating additives such as accelerator, suppressor and leveler. The electrolyte in the anode compartment 208 may be a virgin makeup solution (VMS), for example containing water, copper sulfate, sulfuric acid, and chloride. In certain embodiments, the electrolyte present in the anode compartment 208 includes just water and acid. The use of organic-additive-free electrolyte in the anode compartment 208 is especially beneficial where an active/consumable anode is used.

In an alternative implementation, the anode and working electrode are housed within separate containers that are connected via a salt bridge. In another embodiment, the anode is not separated from the working electrode/test solution.

A seal 212 around the periphery of the upper wall of the anode compartment 208 prevents transfer and leakage of fluid during all the various process steps, and addition and removal of fluids from the chamber. Electrical lead 230 carries current between the anode and the power supply and seals at the anode chamber 208. Electrical lead 235 carries current between the working electrode 201 and the power supply. Reference electrode 221 (e.g., an Hg/HgSO$_4$ reference electrode) is also immersed in and in ionic communication with the electrolyte contained within the cell, and is electrically connected to the power supply via lead 213 (the power supply may be capable of continuously monitoring or controlling the voltage between the working electrode and the reference electrode). A drain and valve assembly 218 at the base of the cell container may be activated via a data collection and process controlling computer 215. The data collection computer 215, sometimes referred to as a controller, is in communication with and controls the programmable potentiostat/galvanostat 214 and sends results of the analysis for display. The computer 215 may also be in communication with a bath control and dosing apparatus on the tool (not shown) via communication line 216. The first and second experiments may be performed in the same cell, or in different cells.

Figure 2B:
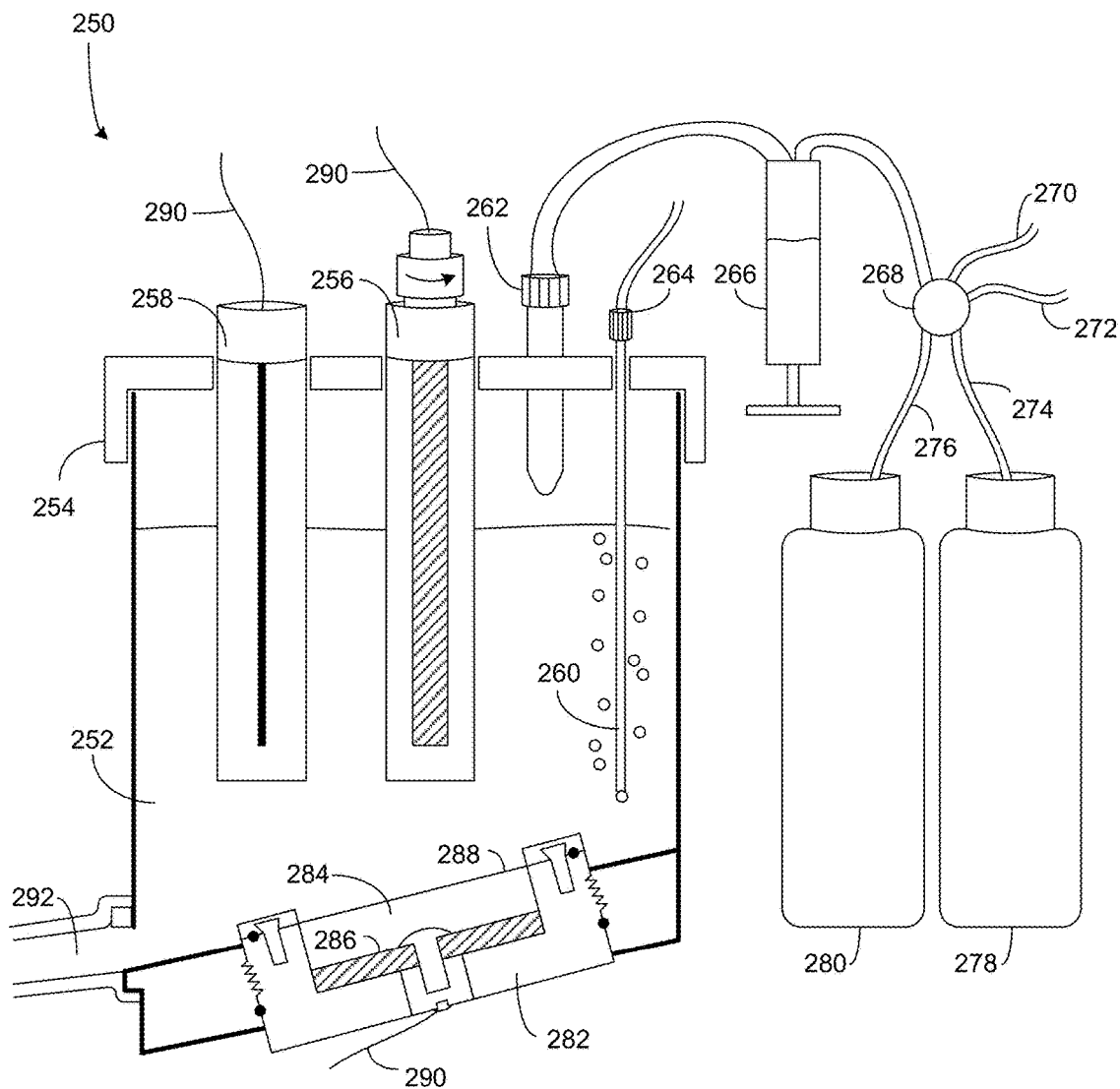
FIG. 2B shows a metrology tool that may be integrated with an electroplating apparatus according to another disclosed embodiment.

FIG. 2B presents an alternative embodiment of a metrology tool 250 that may be integrated with an electroplating apparatus or system (not shown). For example, the metrology tool 250 may be integrated with a multi-tool electroplating apparatus such as a SABRE® family of electroplating tools available from Lam Research Corporation of Fremont, Calif. The metrology tool 250 includes an analysis chamber 252 with lid 254. The lid may be loosely fitting in certain cases, and tightly fitting (e.g., gas-tight) in other cases. The lid 254 has a number of holes to accommodate certain pieces of equipment such as the working electrode 256, a reference electrode 258, a sparge tube 260, and fluid inlet 262. Where a gas-tight lid is desired, each of these holes may include appropriate seals. Gas-tight lids may be beneficial where the analysis chamber is run under vacuum conditions, or where the analysis chamber uses an inert gas blanket. The vacuum conditions and inert gas blanket may be beneficial in minimizing dissolved gases (e.g., oxygen) in the test bath solution. The working electrode 256 may be a rotating electrode with an active area made of platinum, for example. The reference electrode 258 may be an $Hg/Hg_2SO_4$ or an Ag/AgCl reference electrode in certain cases. The sparge tube 260 may provide nitrogen ($N_2$) or other inert gas to the analysis chamber 252. The sparge tube 260 is connected with an inert gas inlet 264. The fluid inlet 262 is connected to a system that is configured to provide all of the relevant fluids for performing the analysis and cleaning the analysis chamber 252. In the embodiment of FIG. 2B, the fluid inlet 262 is connected with a fluid syringe pump 266, which is connected with a multi-position valve 268.

The multi-position valve 268 is connected with various fluid lines including deionized water line 270, bath sample line 272, virgin makeup solution (VMS) line 274, and acceleration solution line 276. The deionized water line 270 is connected with a deionized water source (not shown). The deionized water may be used for cleaning the analysis chamber 252, as well as any components in the analysis chamber 252. The bath sample line 272 may be connected with a port on an electroplating apparatus (not shown) to sample electrolyte directly from a relevant plating bath. In one example, the bath sample line 272 connects with an electroplating chamber. In another example, the bath sample line 272 connects with an electrolyte storage reservoir that is used by a number of electroplating modules. The VMS line 274 is connected with a reservoir of VMS 278, and the acceleration solution line 276 is connected with a reservoir of acceleration solution 280. The VMS reservoir 278 and acceleration solution reservoir 280 are not shown to scale, and in many embodiments these reservoirs are substantially larger. The acceleration solution 280 typically has a high concentration of accelerator, as described herein, and is used for pre-accelerating the working electrode 256 during the analysis.

The metrology tool 250 further includes a counter electrode assembly 282, which includes a separated electrode chamber 284 housing counter electrode 286. The counter electrode 286 may be a copper electrode, for example a phosphorus-doped copper electrode, or it may be an inert electrode. The separated electrode chamber 284 is separated from the rest of the analysis chamber 252 by a membrane 288. The membrane 288 may be an ion exchange membrane or a microporous membrane, for example. A drain 292 may be provided near the bottom of the analysis chamber 252. The drain may further include a valve (not shown) to allow fluid to collect and drain in the analysis chamber 252 as desired. As shown in the embodiment of FIG. 6B, the bottom of the analysis chamber 252 may be slanted downwards toward the drain to improve drainage.

Wiring 290 is used to electrically connect various components to a controller (not shown). For instance, the wiring 290 may connect the controller with the working electrode 256, the reference electrode 258, and the anode 286. Additional wiring may be provided to control other components such as the multi-position valve 272, fluid syringe pump 266, and drain 292. The controller (not shown) may be a local controller that regulates the various components of the metrology tool 250, or it may be a global controller that regulates a number of different processes on a multi-tool electroplating apparatus.

In some cases, the metrology tool 250 may be modified to include certain additional elements. In one embodiment, the metrology tool includes an acceleration chamber, separate from the analysis chamber, in which the pre-acceleration of the working electrode takes place. Where this is the case, the reservoir for acceleration solution may be connected with the acceleration chamber. Further, a mechanism for moving the working electrode between the acceleration chamber and the analysis chamber may be provided. Such a mechanism may involve a robotic transfer arm or other transfer mechanism as known in the art. The transfer mechanism may move the working electrode itself, or may move the relevant chambers into which the working electrode is inserted (i.e., the transfer mechanism may allow the working electrode to remain stationary while the acceleration chamber and analysis chamber rotate/translate to engage the working electrode). The use of a separate pre-acceleration chamber may be beneficial where the analysis chamber is constructed from a material that adsorbs accelerator. Where the analysis chamber is made from an unreactive material, such as glass, or one that otherwise does not adsorb accelerator, the use of a separate acceleration chamber is unnecessary.

Another feature that may be combined with any of the embodiments described herein is an additional reservoir and fluid line for providing etching solution to the analysis chamber. The etching solution may be used to remove electrodeposited material from the working electrode between subsequent experiments/processes. The etching solution line may connect with the multi-position valve 268 shown in FIG. 2B, or it may otherwise connect with the fluid inlet 262 or another inlet, as desired. Where a distinct etching solution is provided to the analysis chamber, the analysis chamber should be rinsed (e.g., with deionized water or another rinse solution) before other solutions are introduced. Likewise, where a distinct etching solution is provided to etch the working electrode, the electrode should be rinsed before subsequent processing steps. The etching solution may be provided to the analysis chamber in series with the other relevant solutions (e.g., test bath solution, acceleration solution and rinse solution). In other embodiments, chemical etching of the working electrode may occur in a separate etching chamber. A mechanism may be provided for moving the working electrode into the etching chamber, or for moving the relevant chambers to engage the working electrode, as described above in relation to the acceleration chamber.

In various embodiments, it is not necessary to provide etching solution to the analysis chamber. For example, removal of material from the working electrode may instead occur through electrochemical etching, which involves applying a reverse current to the working electrode and deplating the material thereon. Such electrochemical etching does not require a distinct etching solution. Rather, the electrochemical etching occurs in the available electrolyte (e.g., test bath solution or other electrolyte supply).

A further feature that may be combined with any of the disclosed embodiments is a mechanism for regulating the amount of dissolved gas (e.g., oxygen) in the test bath solution. Such regulation may be accomplished by stripping (i.e., bubbling nitrogen through the solution to remove oxygen, as in the case shown in FIG. 2B) in some cases. In other cases, the test bath solution may be delivered to the analysis chamber in a de-gassed state. In this instance, degassing of the test bath solution may occur on an electroplating apparatus (e.g., a multi-tool electroplating apparatus), and the solution should be provided to the analysis chamber without introducing additional gasses. In one example, degassed test bath solution is delivered from an electroplating apparatus to an analysis chamber that is under vacuum. The vacuum helps prevent the test bath solution from being exposed to oxygen or other gases that could dissolve in the test bath solution. In another example, degassed test bath solution is delivered from an electroplating apparatus to an analysis chamber that contains a nitrogen blanket or other inert gas blanket.

As mentioned, the metrology tool may be a standalone tool, or it may be incorporated into a multi-tool electroplating apparatus. In either case, data collected by the metrology tool may be processed by a controller/processor that is local to the metrology tool, or by a controller/processor that is part of a multi-tool apparatus. Where data analysis is performed on a multi-tool apparatus, the metrology tool (whether standalone or incorporated into a multi-tool apparatus) should include a communication line (e.g., a wired or wireless data connection) for transmitting the data gathered on the metrology tool to the relevant controller/processor of the multi-tool apparatus. In this embodiment, the multi-tool apparatus may also be considered an analysis system, as the metrology data is being analyzed directly on the multi-tool apparatus.

The controller may have instructions to determine whether the additives of the electroplating bath of interest (the test bath solution) meet a defined electroplating specification. In various cases, the defined electroplating specification relates to achieving bottom-up fill within a desired timeframe. Other electroplating specifications may be chosen, as well. In order to make such a determination, the controller may have instructions to perform the experiments and analysis described herein. For example, the controller may have instructions to flow various fluids into the analysis chamber in series. In one example, the controller has instructions to sequentially flow virgin makeup solution (VMS) into the analysis chamber and plate the working electrode with a standardized copper (or other metal) layer, drain the analysis chamber, rinse the analysis chamber, flow test bath solution into the analysis chamber and contact the working electrode with the test bath solution, perform a first electrochemical experiment and record a first output as described herein, apply a reverse current to the working electrode to remove material from the working electrode, drain and rinse the analysis chamber, flow VMS into the analysis chamber and plate the working electrode with a standardized copper (or other metal) layer, drain the analysis chamber, flow acceleration solution into the analysis chamber and contact the working electrode with acceleration solution until the working electrode is substantially fully accelerated, drain the analysis chamber, rinse the analysis chamber and working electrode, flow test bath solution into the analysis chamber and contact the working electrode with the test bath solution, perform a second electrochemical experiment and record a second output as described herein, and analyze the first and/or second output to determine whether the additives of the test bath solution meet the defined electroplating specification. In some cases, the controller may have instructions to plate material onto the working electrode while the working electrode is immersed in the acceleration solution. These instructions may replace instructions to plate the working electrode with metal in the VMS solution before contacting the working electrode with accelerator solution.

Where the metrology tool includes additional chambers for performing the pre-acceleration and/or etching, the controller may further include instructions for transferring the working electrode with respect to the relevant chambers/containers.

The controller may have instructions to perform the first electrochemical experiment by applying a first controlled current to the working electrode and measuring a first potential of the electrode over time. The controller may have instructions to perform the second electrochemical experiment by applying a second controlled current to the working electrode and measuring a second potential of the electrode over time. Alternatively, the controller may have instructions to perform the second electrochemical experiment by applying a controlled voltage to the working electrode and measuring a current experienced by the electrode over time. The controller may have instructions to apply a controlled voltage that is derived from the first experiment.

The controller may have instructions to analyze the first and second outputs by analyzing various characteristics of the outputs of the first and second experiment. For instance, the controller may have instructions to analyze the outputs by comparing a current density output of the second experiment at a relevant time to a threshold current density. In another case, the controller may have instructions to analyze the outputs by comparing the time at which the current density output of the second experiment crosses a threshold current density. The controller may also have instructions to analyze the outputs by comparing the integrated current density output from the second experiment over a relevant time period, to a threshold value of charge per area. In yet another embodiment, the controller may have instructions to analyze the outputs by comparing a threshold ratio to a ratio of the voltage output of the first experiment at a first time to the voltage output of the second experiment at a second time.

In some embodiments, a flow through cell may be used in place of the apparatus described above and shown in FIGS. 2A and 2B. Such flow through cells are further discussed and described in U.S. Pat. No. 8,372,258, filed Aug. 3, 2009, and titled "MONITORING OF ELECTROPLATING ADDITIVES," issued to Mark J. Willey et. al, such application being incorporated by reference herein in its entirety. The various processes of pre-plating, and pre-chemical or electrochemically treating the pre-plated surfaces are largely unchanged, but the apparatus form and flow pattern (e.g., the use of a flow channel rather than a rotating disc) are different. In some cases, the flow through cell may have advantages over the aforementioned RDE based design for in line monitoring simplicity or for reducing test bath fluid volume requirements. As would be obvious to one skilled in the art, all necessary ancillary hardware and feed supply routing of additive-free plating solution, accelerator solutions, rinsing solution, etching solution, and standards would be added as required to enable the processes described above to be performed appropriately in the flow through cell.

In some cases, the electrochemical cell is integrated into an electroplating platform such as the Sabre™ system available from Lam Research Corporation of Fremont, Calif.

Figure 3:
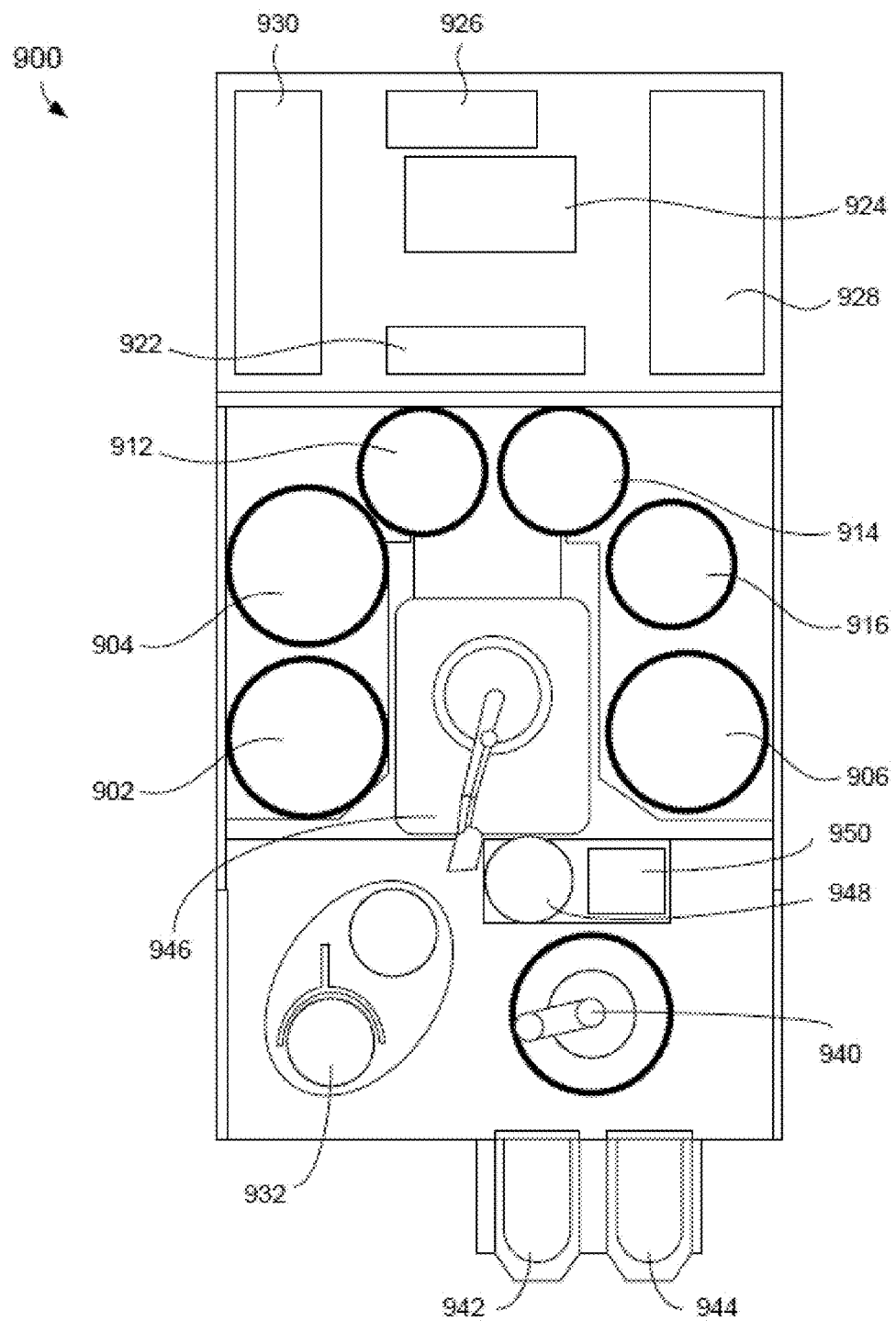
FIGS. 3 and 4 show example multi-tool apparatuses that may be used in accordance with certain embodiments.

FIG. 3 shows an example of a multi-tool semiconductor processing apparatus that may be used to implement the techniques disclosed herein. The electrodeposition apparatus 900 can include three separate electroplating modules 902, 904, and 906. The electrodeposition apparatus 900 can also include a solution analysis module 916. Further, two separate modules 912 and 914 may be configured for various process operations. For example, in some embodiments, one or more of modules 912 and 914 may be a spin rinse drying (SRD) module. In other embodiments, one or more of the modules 912 and 914 may be post-electrofill modules (PEMs), each configured to perform a function, such as edge bevel removal, backside etching, and acid cleaning of substrates after they have been processed by one of the electroplating modules 902, 904, and 906.

The electrodeposition apparatus 900 includes a central electrodeposition chamber 924. The central electrodeposition chamber 924 is a chamber that holds the chemical solution used as the electroplating solution in the electroplating modules 902, 904, and 906. The electrodeposition apparatus 900 also includes a dosing system 926 that may store and deliver additives for the electroplating solution. A chemical dilution module 922 may store and mix chemicals, for example for use with an etchant or other solution. A filtration and pumping unit 928 may filter the electroplating solution for the central electrodeposition chamber 924 and pump it to the electroplating modules.

A system controller 930 provides electronic and interface controls to operate the electrodeposition apparatus 900. The system controller 930 is further discussed below.

In some embodiments, there may be a user interface associated with the system controller 930. The user interface may include a display screen, graphical software displays of the apparatus and/or process conditions, and user input devices such as pointing devices, keyboards, touch screens, microphones, etc.

Signals for monitoring the process may be provided by analog and/or digital input connections of the system controller 930 from various process tool sensors. The signals for controlling the process may be output on the analog and digital output connections of the process tool. Non-limiting examples of process tool sensors that may be monitored include mass flow controllers, pressure sensors (such as manometers), thermocouples, optical position sensors, etc. Appropriately programmed feedback and control techniques may be used with data from these sensors to maintain process conditions.

In one embodiment of a multi-tool apparatus, the instructions can include inserting the substrate in a wafer holder, tilting the substrate, biasing the substrate during immersion, and electrodepositing a copper containing structure on a substrate. The instructions may further include transferring solution from an electroplating cell or the central electrodeposition chamber 924 to the solution analysis module 916, applying a designated current-controlled waveform, measuring and recording a potential output, applying rinsing solution to an electrode, performing an etching operation to recover the working electrode, transferring concentrated accelerator solution to the solution analysis module to saturate the working electrode surface with accelerator, applying a controlled potential to the working electrode based on a potential output of a previous experiment, measuring and recording a current density output, analyzing the potential and current density outputs to predict whether a particular bath is capable of satisfactorily filling a recessed feature, alerting an operator when a bath is found to be unsuitable, shutting down a plating apparatus when a bath is found to be unsuitable, and directing an additive control mechanism to automatically adjust the composition of a plating solution based on the potential and current density outputs described above (and also optionally based on other metrology results such as tests analyzing specific concentration levels of certain bath components, such as the conventional metrology methods mentioned herein).

A hand-off tool 940 may select a substrate from a substrate cassette such as the cassette 942 or the cassette 944. The cassettes 942 or 944 may be front opening unified pods (FOUPs). A FOUP is an enclosure designed to hold substrates securely and safely in a controlled environment and to allow the substrates to be removed for processing or measurement by tools equipped with appropriate load ports and robotic handling systems. The hand-off tool 940 may hold the substrate using a vacuum attachment or some other attaching mechanism.

The hand-off tool 940 may interface with a wafer handling station 932, the cassettes 942 or 944, a transfer station 950, or an aligner 948. From the transfer station 950, a hand-off tool 946 may gain access to the substrate. The transfer station 950 may be a slot or a position from and to which hand-off tools 940 and 946 may pass substrates without going through the aligner 948. In some embodiments, however, to ensure that a substrate is properly aligned on the hand-off tool 946 for precision delivery to an electroplating module, the hand-off tool 946 may align the substrate with an aligner 948. The hand-off tool 946 may also deliver a substrate to one of the electroplating modules 902, 904, or 906, or to one of the separate modules 912 and 914 configured for various process operations.

An apparatus configured to allow efficient cycling of substrates through sequential plating, rinsing, drying, and PEM process operations (such as stripping) may be useful for implementations for use in a manufacturing environment. To accomplish this, the module 912 can be configured as a spin rinse dryer and an edge bevel removal chamber. With such a module 912, the substrate would only need to be transported between the electroplating module 904 and the module 912 for the copper plating and EBR operations.

Figure 4:
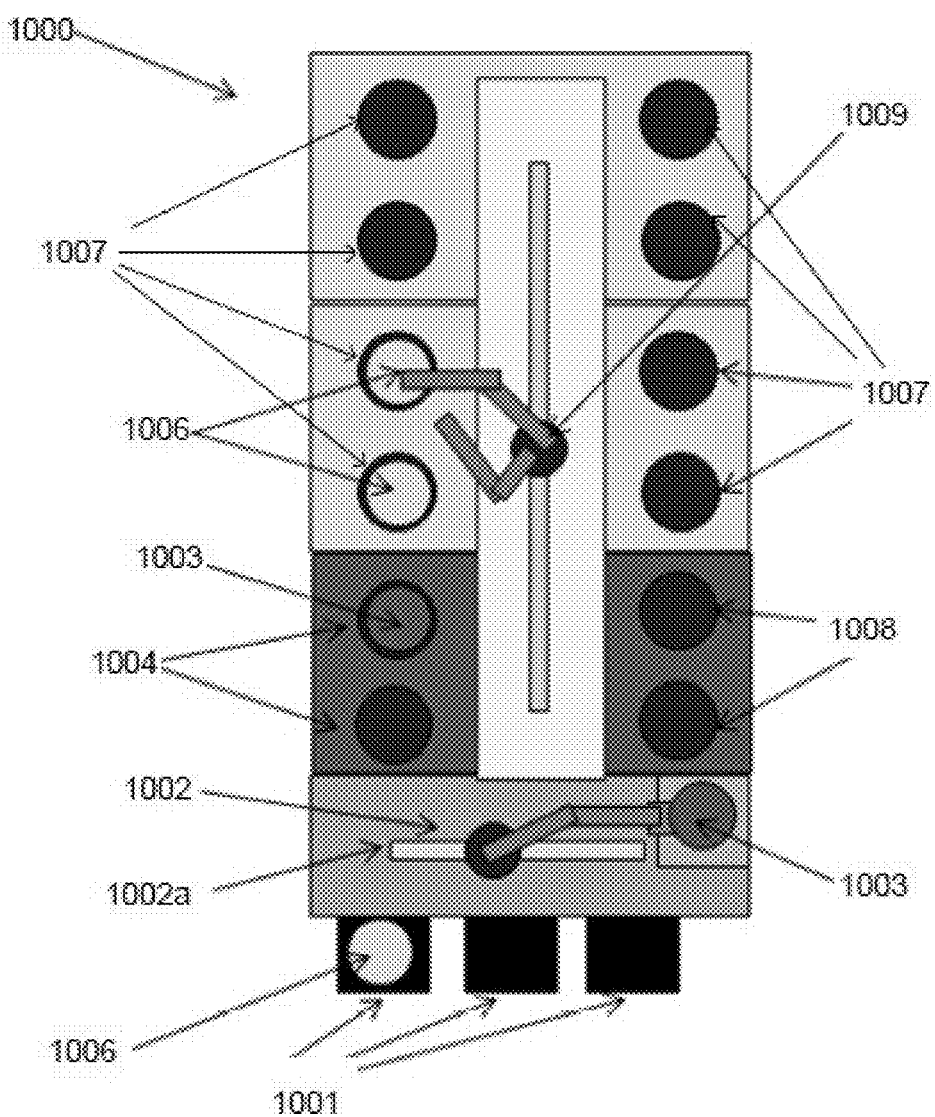

FIG. 4 shows an alternative example of a multi-tool apparatus that may be used in conjunction with an appropriate metrology tool. In this embodiment, the electrodeposition apparatus 1000 has a set of electroplating cells 1007, each containing an electroplating bath, in a paired or multiple "duet" configuration. In addition to electroplating per se, the electrodeposition apparatus 1000 may perform a variety of other electroplating related processes and sub-steps, such as spin-rinsing, spin-drying, metal and silicon wet etching, electroless deposition, pre-wetting and pre-chemical treating, reducing, annealing, photoresist stripping, surface pre-activation, and solution analysis, for example. The electrodeposition apparatus 1000 is shown schematically looking top down in FIG. 4, and although only a single level or "floor" is revealed in the figure, it is to be readily understood by one having ordinary skill in the art that such an apparatus, e.g. the Lam Research Sabre™ 3 D tool, can have two or more levels "stacked" on top of each other, each potentially having identical or different types of processing stations.

Referring once again to FIG. 4, the substrates 1006 that are to be electroplated are generally fed to the electrodeposition apparatus 1000 through a front end loading FOUP 1001 and, in this example, are brought from the FOUP to the main substrate processing area of the electrodeposition apparatus 1000 via a front-end robot 1002 that can retract and move a substrate 1006 driven by a spindle 1003 in multiple dimensions from one station to another of the accessible stations—two front-end accessible stations 1004 and also two front-end accessible stations 1008 are shown in this example. The front-end accessible stations 1004 and 1008 may include, for example, pre-treatment stations, and spin rinse drying (SRD) stations. These stations 1004 and/or 1008 may also be solution analysis modules as described herein.

Lateral movement from side-to-side of the front-end robot 1002 is accomplished utilizing robot track 1002*a*. Each of the substrates 1006 may be held by a cup/cone assembly (not shown) driven by a spindle 1003 connected to a motor (not shown), and the motor may be attached to a mounting bracket 1009. Also shown in this example are the four "duets" of electroplating cells 1007, for a total of eight electroplating cells 1007. The electroplating cells 1007 may be used for electroplating copper for a copper containing structure and electroplating solder material for a solder structure (among other possible materials). A system controller (not shown) may be coupled to the electrodeposition apparatus 1000 to control some or all of the properties of the electrodeposition apparatus 1000. The system controller may be programmed or otherwise configured to execute instructions according to processes described earlier herein.

System Controller

In some embodiments, a system controller (which may include one or more physical or logical controllers) controls some or all of the operations of a process tool. The system controller will typically include one or more memory devices and one or more processors. The processor may include a central processing unit (CPU) or computer, analog and/or digital input/output connections, stepper motor controller boards, and other like components. Instructions for implementing appropriate control operations are executed on the processor. These instructions may be stored on the memory devices associated with the controller or they may be provided over a network. In certain embodiments, the system controller executes system control software.

The system control software may include instructions for controlling the timing, mixture of electrolyte components, inlet pressure, electrochemical cell pressure, electrochemical cell temperature, electrode temperature, current and potential applied to the working electrode and any other electrodes, electrode position, electrode rotation, electrode immersion speed, experimental result analysis, and other parameters of a particular process performed by the process tool. System control software may be configured in any suitable way. For example, various process tool component subroutines or control objects may be written to control operation of the process tool components necessary to carry out various process tool processes. System control software may be coded in any suitable computer readable programming language.

In some embodiments, system control software includes input/output control (IOC) sequence instructions for controlling the various parameters described above. For example, each phase of a bath analysis process may include one or more instructions for execution by the system controller. The instructions for setting process conditions for an immersion process phase may be included in a corresponding immersion recipe phase. In some embodiments, the bath analysis recipe phases may be sequentially arranged, so that all instructions for a bath analysis process phase are executed concurrently with that process phase.

Other computer software and/or programs may be employed in some embodiments. Examples of programs or sections of programs for this purpose include an electrode positioning program, an electrolyte composition control program, a pressure control program, a heater control program, and a potential/current power supply control program.

In some cases, the controllers control one or more of the following functions: electrode immersion, fluid transfer between tanks, experimental result analysis, etc. The electrode immersion may be controlled by, for example, directing an electrode lift assembly, electrode tilt assembly and/or electrode rotation assembly to move as desired. The controller may control the fluid transfer between tanks by, for example, directing certain valves to be opened or closed and certain pumps to turn on and off. The controller may execute experimental result analysis by applying the techniques related above (or similar techniques) to the data generated by performing the first and second experiment. Further, the controller may control the potential applied during the second experiment based on the output of the first experiment. The controller may also be configured to report the results of the experiments. Such reports can include sending an alarm to an operator, or stopping or slowing production in an electroplating apparatus. In some cases the controller may be programmed/configured to provide automatic adjustment of plating bath chemistry (e.g., in conjunction with a dosing system) based on the output of the experiments described herein, and optionally based as well on other metrology results such as those testing the concentration of individual components in the bath. In various cases the controller may provide such reports/adjustments with the goal of improving the plating properties of the electrolyte solution. The controllers may control these aspects based on sensor output (e.g., when current, current density, potential, pressure, etc. reach a certain threshold), the timing of an operation (e.g., opening valves at certain times in a process) or based on received instructions from a user.

The various hardware and method embodiments described above may be used in conjunction with lithographic patterning tools or processes, for example, for the fabrication or manufacture of semiconductor devices, displays, LEDs, photovoltaic panels and the like. Typically, though not necessarily, such tools/processes will be used or conducted together in a common fabrication facility.

Lithographic patterning of a film typically comprises some or all of the following steps, each step enabled with a number of possible tools: (1) application of photoresist on a workpiece, e.g., a substrate having a silicon nitride film formed thereon, using a spin-on or spray-on tool; (2) curing of photoresist using a hot plate or furnace or other suitable curing tool; (3) exposing the photoresist to visible or UV or x-ray light with a tool such as a wafer stepper; (4) developing the resist so as to selectively remove resist and thereby pattern it using a tool such as a wet bench or a spray developer; (5) transferring the resist pattern into an underlying film or workpiece by using a dry or plasma-assisted etching tool; and (6) removing the resist using a tool such as an RF or microwave plasma resist stripper. In some embodiments, an ashable hard mask layer (such as an amorphous carbon layer) and another suitable hard mask (such as an antireflective layer) may be deposited prior to applying the photoresist.

It is to be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated may be performed in the sequence illustrated, in other sequences, in parallel, or in some cases omitted. Likewise, the order of the above described processes may be changed.

The subject matter of the present disclosure includes all novel and nonobvious combinations and sub-combinations of the various processes, systems and configurations, and other features, functions, acts, and/or properties disclosed herein, as well as any and all equivalents thereof.

Experimental

Experimental results have shown that the disclosed techniques may be used to accurately predict the ability of a bath to fill a TSV feature. The experiments tested four different baths: three baths that were known produce an incomplete fill according to various known failure modes, and one bath that was known to produce a complete and satisfactory fill. The failure modes were chosen to represent types of failure that are not detectable by conventional methods measuring for known breakdown products.

Failed Bath 1 failed due to a loss of acceleration of the feature near the end of the filling process. One mechanism for causing this failure is the presence of an accelerator deactivating agent in the bath, which causes the current within the feature to drop prior to the metal fully filling the feature. The precise mechanism by which Failed Bath 2 is unsuccessful is unknown. Failed Bath 3 failed due to the presence of trace levels (less than about 1 ppm) of hydrogen peroxide. FIGS. 8A-8D show TSV features plated in Failed Baths 1-3 and Successful Bath 4, respectively.

The first and second experiments were performed using a benchtop apparatus that allowed temperature tuning, degassing, and circulation of a 1 L test solution. In each case, the counter electrode was separated from the test solution by a cationic membrane (a NAFION® membrane from DuPont), and was immersed in an additive-free solution of copper sulfate and acid. Each experiment was run for approximately 1 hour.

The first experiment was performed multiple times for each test solution. The experiment employed a 5 mm diameter platinum RDE that was pre-plated with copper in an additive free solution of about 1 mol/L $CuSO_4$, about 0.6 mol/L $H_2SO_4$, and about 50 ppm HCl at about 23° C. for about 1 minute and 6 seconds. The RDE was rotated at a rate of about 20 RPM. The other plating conditions (including the waveform, which was a constant 1.25 $mA/cm^2$) were chosen to simulate those in a typical substrate plating process known to achieve a full feature filling when used with a successful HSL plating bath supplied by MLI Industries of Moses Lake, Wash.

Figure 5:
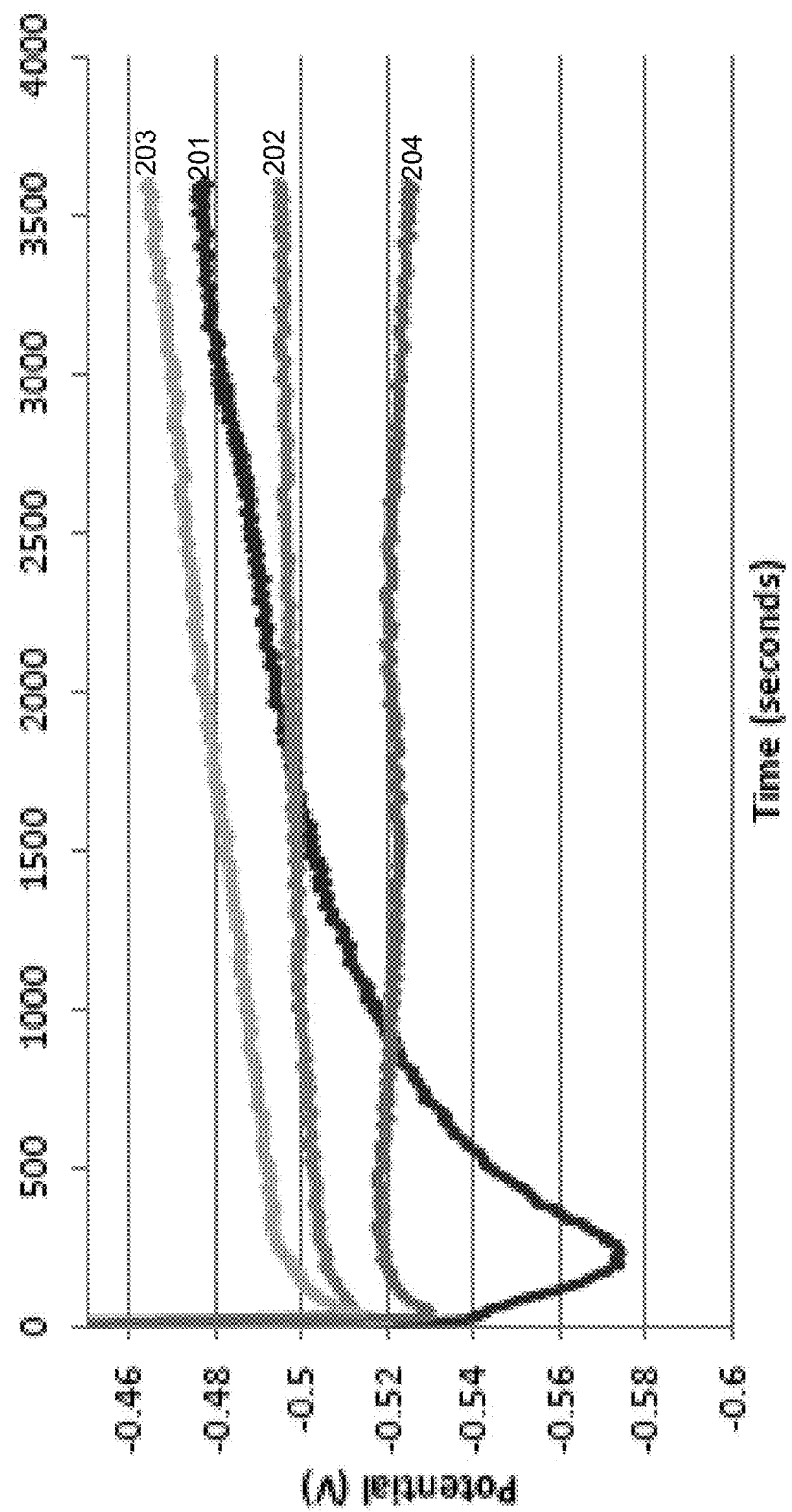
FIG. 5 is a chart showing the results (potential vs. time) of a current-controlled experiment.

FIG. 5 shows the results (potential (V) vs. time (s)) from the first experiment for each of the four test baths. Line 201 corresponds to Failed Bath 1, line 202 corresponds to Failed Bath 2, line 203 corresponds to Failed Bath 3, and line 204 corresponds to Successful Bath 4. Each of the three failed baths were designed to result in types of failure that are undetectable through conventional methods.

The second experiment was performed multiple times for each test solution, and two different sized RDEs were tested. The first RDE had a diameter of about 5 mm, and the second RDE had a diameter of about 0.433 mm. Each electrode was pre-plated with copper in a solution that was similar to the one employed for pre-plating the electrode in the first experiment, but with the addition of about 100× the concentration of accelerator typically used for plating. This pre-plating procedure produced RDEs which were saturated with accelerator. Each RDE was tested at 0 RPM and 2500 RPM to evaluate mass transport differences and provide replicate measurements.

The second experiment was performed in a potentiostatic mode. The applied potential was chosen based on the average of the potential applied over about the final 10 minutes of the first experiment, for each particular solution. The other plating conditions were equivalent to those used in the first experiment, with the exception of electrode surface area and rotation rate, as mentioned above.

Figure 6:
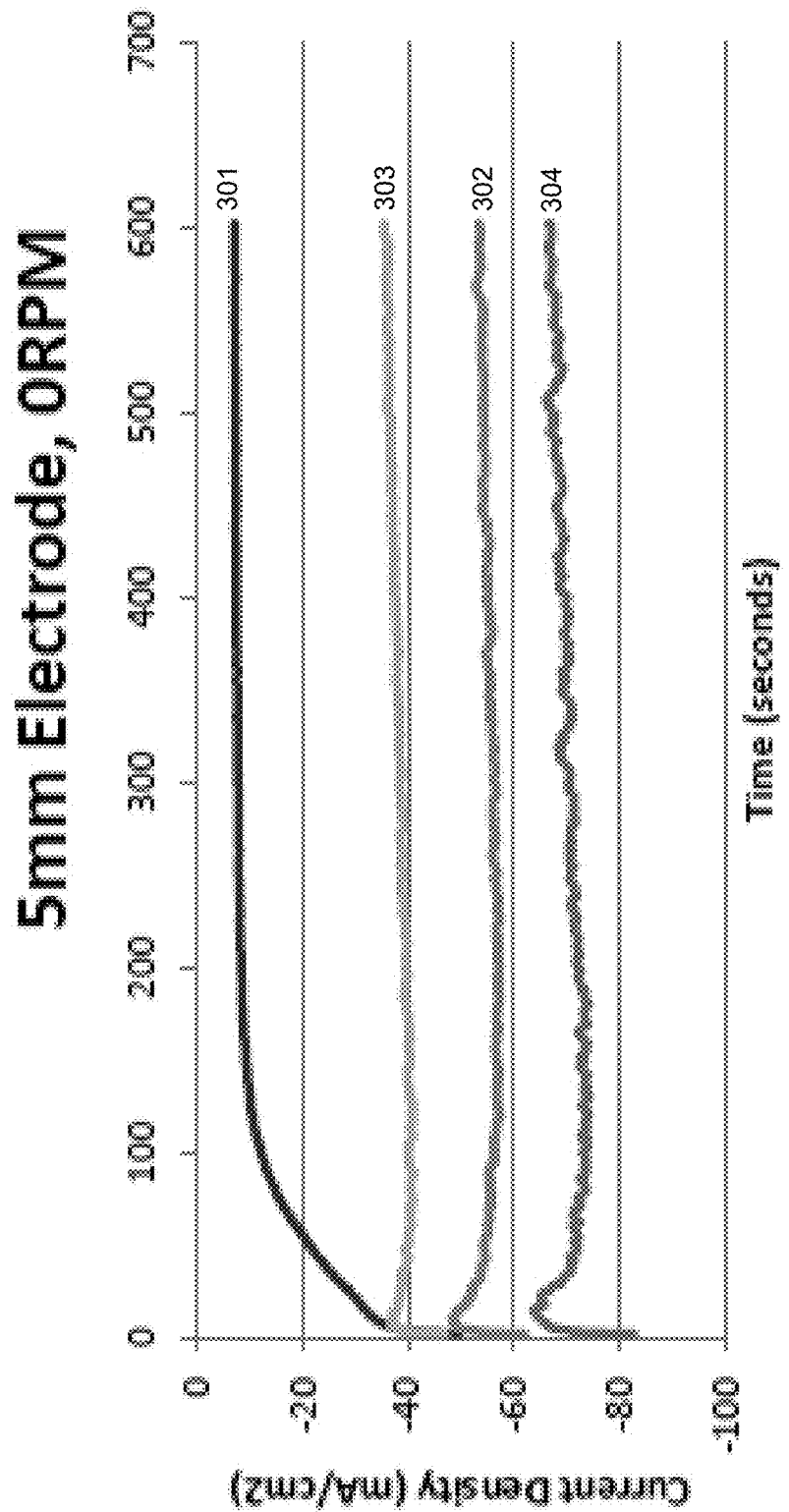
FIGS. 6 and 7 are charts showing the results (current density vs. time) of potential controlled experiments performed at different conditions.
Figure 7:
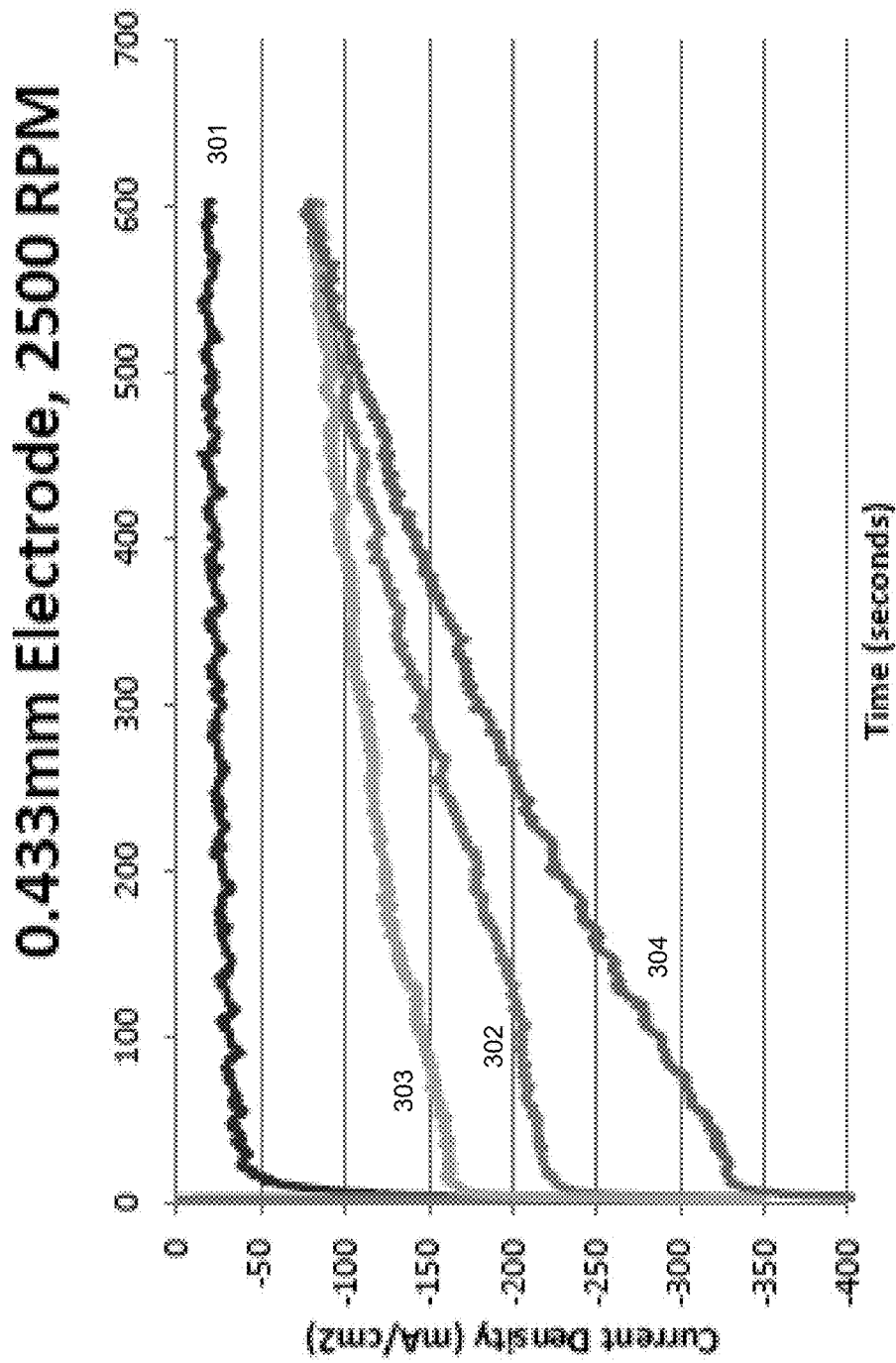

FIGS. 6 and 7 show the results (current density ($mA/cm^2$) vs. time(s)) for the second experiments. FIG. 6 relates to results for the 5 mm electrode at 0 RPM and FIG. 7 relates to the results for the 0.433 mm electrode at 2500 RPM. For the sake of brevity, only these two cases (which are on the extreme ends of the mass transport cases) are shown. In each figure, line 301 corresponds to Failed Bath 1, line 302 corresponds to Failed Bath 2, line 303 corresponds to Failed Bath 3, and line 304 corresponds to Successful Bath 4. The current density results of the second experiment show that the current density for the failed baths was lower (less negative) than the current density of the good bath. When high convective conditions are used (i.e., in the 2500 RPM case), the current densities for the different solutions all seem to trend towards approximately the same value. This apparent convergence of the data at late times at high RPM is indicative of an accelerator shut down mechanism typically attributed to the presence of an accelerator-deactivating compound that inhibits or stops the fill in the features after the fill is complete and begins to overfill the feature. These accelerator-deactivating compounds are functionally referred to as levelers, and they are typically diffusion limited.

The resulting data was used in relation to the techniques presented above in order to empirically determine appropriate threshold results for the tested plating system, and further, to evaluate the ability of the techniques to accurately predict whether the a bath will be successful in producing an adequate feature fill.

Tables 1-3, presented in FIGS. 9A-9C, relate to the results from Techniques 1-3, respectively, for each of the 4 test solutions. Each table indicates the particular RDE electrode used and the RPM at which the RDE was rotated. The tables also indicate the threshold values that were chosen for each case, and at what point (e.g., at what time(s), or at what current density) the measurements were taken. The numbers related in each Bath column correspond to the output of the technique being used. For example, for Table 1 in FIG. 9A (Technique 1), the Failed Bath 1 column is calculated as the absolute value of the output of the second experiment (current density) for Failed Bath 1 at the time indicated in the Time column. Similarly, for Table 2 in FIG. 9B (Technique 2), the Failed Bath 1 column is calculated as the time at which the absolute value of the output of the second experiment for Failed Bath 1 crosses the designated current density threshold, as related in the $CD_{th}$ column. For Table 3 in FIG. 9C, the Failed Bath 1 column is calculated as the absolute value of the definite integral of the output of the second experiment, evaluated over the period $t_1$-$t_2$. In Tables 1-3, solutions that "pass" the technique (i.e., solutions for which the technique predicts the bath will be successful) are included in boxes that are highlighted in gray. The highlighting is included for clarity, although the same information can be gleaned by comparing the values listed for each Bath to the threshold condition for that particular case.

The results in Tables 1-3 show that the disclosed techniques may be used to accurately predict the ability of a particular bath to produce a satisfactory fill result. For each case, threshold values could be chosen to reliably distinguish between baths that will be successful and baths that will fail.

Figure 8A:
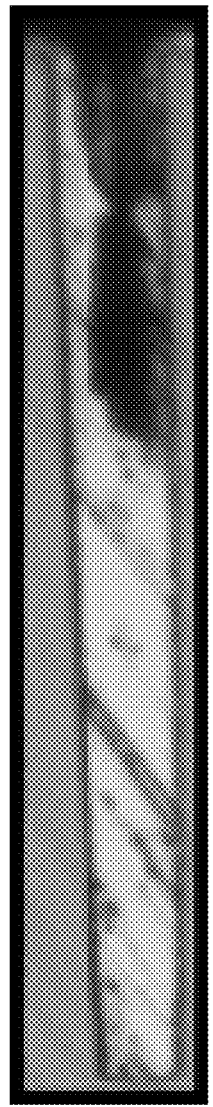
FIGS. 8A-8D show cross-sectional images of 10×100 μm TSV features filled in the baths evaluated in FIGS. 5-7.
Figure 8B:
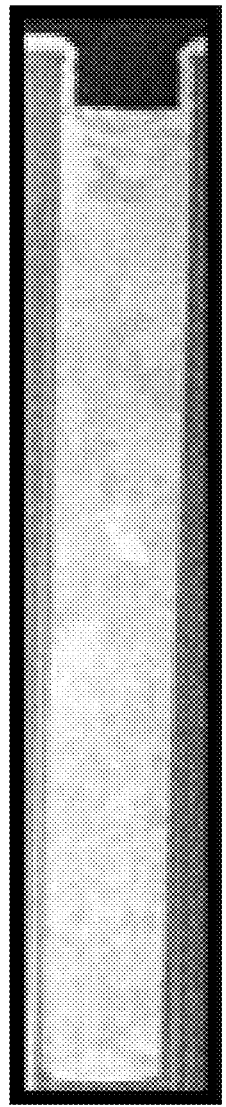
Figure 8C:
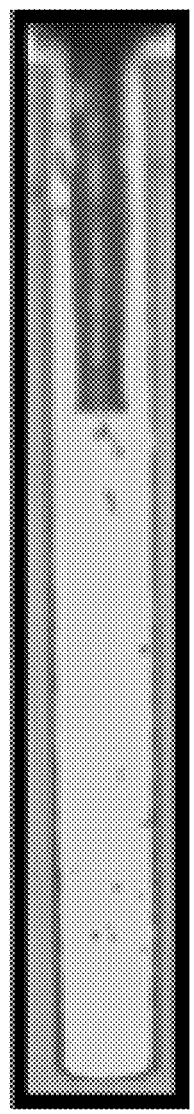
Figure 8D:
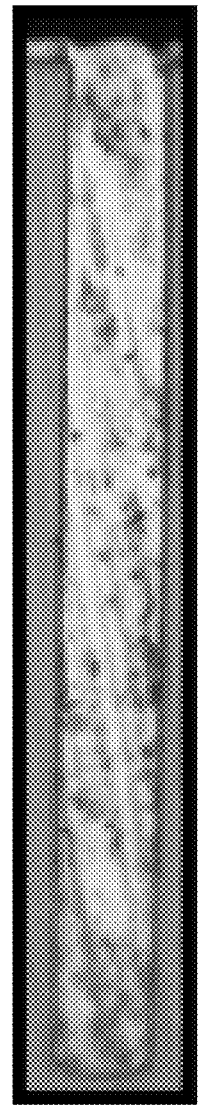

FIGS. 8A-8D show cross-sectional images of 10×100 μm TSV features plated in the baths evaluated in FIGS. 2A-4 and Tables 1-3. Specifically, FIG. 8A shows a feature plated in Failed Bath 1, FIG. 8B shows a feature plated in Failed Bath 2, FIG. 8C shows a feature plated in Failed Bath 3, and FIG. 8D shows a feature plated in Successful Bath 4. The only feature that was completely filled was the one plated in Successful Bath 4.

What is claimed is:

1. A method of evaluating whether additives in an electroplating bath of interest meet an electroplating specification, the method comprising:

performing a first experiment by:
   contacting an electrode with the electroplating bath of interest,
   applying a current density waveform to the electrode, wherein the current density waveform applied approximates a current density experienced in a field region of a substrate when electroplated in the electroplating bath of interest, and
   recording a first potential trace output during the first experiment;
performing a second experiment by:
   contacting a second electrode with an acceleration solution comprising accelerator until the second electrode is substantially fully accelerated,
   rinsing the acceleration solution from the second electrode,
   contacting the second electrode with the electroplating bath of interest,
   applying a second current density waveform or a potential waveform to the second electrode, wherein the second current density waveform or potential waveform approximates the current density or potential experienced within a feature on the substrate when electroplated in the electroplating bath of interest,
   where a second current density waveform is applied, recording a second potential trace output during the second experiment, and where a potential waveform is applied to the second electrode, recording a current trace output during the second experiment; and
determining, based on two or more parameters selected from the group consisting of the first potential trace output, the second potential trace output, the current trace output, and calibration data, whether the additives in the electroplating bath of interest meet the electroplating specification.

2. The method of claim 1, wherein the electroplating specification relates to the capability of the additives in the electroplating bath of interest to fully fill the feature on the substrate through a bottom-up mechanism in an acceptable timeframe.

3. The method of claim 1, wherein the current density waveform applied during the first experiment corresponds to a current density waveform used for electroplating material on the substrate in a target filling process.

4. The method of claim 3, wherein the current density waveform applied during the first experiment corresponds to a current density waveform used for electroplating material on the substrate in a target filling process, as modified by a field current density correction factor.

5. The method of claim 3, wherein a rotation rate of the second electrode during the second experiment is higher than a rotation rate of the substrate during the target filling process.

6. The method of claim 3, wherein a temperature of the electroplating bath of interest during the second experiment is higher than a temperature of the electroplating bath of interest during the target filling process.

7. The method of claim 1, wherein the first potential trace output from the first experiment is used to select the potential waveform applied in the second experiment.

8. The method of claim 7, wherein the potential waveform is selected based on the potential experienced during a final period of electroplating during the first experiment.

9. The method of claim 8, wherein the potential waveform is selected based on an average potential of the first potential trace output during a final period of electroplating during the first experiment.

10. The method of claim 7, wherein the first potential trace output from the first experiment is used to calculate a predicted potential, the predicted potential corresponding to a potential that would be experienced if electroplating were to continue after a final electroplating period in the first experiment, and wherein the potential waveform in the second experiment is based on the predicted potential.

11. The method of claim 2, wherein the second current density waveform is selected based on a current density to fully fill the feature in the acceptable timeframe.

12. The method of claim 1, wherein the electrode and the second electrode are the same electrode, and further comprising removing material deposited on the electrode during the first experiment before contacting the electrode with the acceleration solution.

13. The method of claim 1, wherein the determining comprises comparing a current density at a relevant time from the current density trace output from the second experiment to a threshold current density.

14. The method of claim 1, wherein the determining comprises comparing a time at which the current density trace output from the second experiment reaches a threshold current density to a threshold time.

15. The method of claim 1, wherein the determining comprises integrating the current density trace output from the second experiment between a first time and a second time to calculate a charge density, and comparing the charge density to a threshold charge density.

16. The method of claim 1, wherein the determining comprises calculating a ratio between a potential from the first potential trace output at a first time during the first experiment to a potential from the second potential trace output at a second time during the second experiment, and comparing the ratio to a threshold ratio.

17. The method of claim 1, wherein the calibration data is generated by performing the first and/or second experiment on electrolytes that are known to produce acceptable fill results and electrolytes that are known to produce unacceptable fill results.

18. The method of claim 17, wherein the calibration data comprises one or more of the parameters selected from the group consisting of: a threshold current density, a threshold charge density, a threshold time, and a threshold ratio of potentials.

19. The method of claim 2, wherein the acceptable timeframe is about 1 hour or less.

20. The method of claim 1, further comprising electroplating metal onto the electrode before contacting the electrode with the electroplating bath of interest in the first experiment, and electroplating metal onto the second electrode before contacting the second electrode with the acceleration solution.

21. The method of claim 1, wherein a concentration of accelerator in the acceleration solution is at least about 10 times a concentration of accelerator in the electroplating bath of interest.

22. A method of monitoring the additives in an electroplating bath of interest, the method comprising:
   (a) applying a defined current density to a first electrode while in contact with the electroplating bath of interest, wherein the defined current density represents a current density experienced in a field region of a substrate when electroplated in the electroplating bath of interest, and
   wherein the first electrode's surface is not substantially fully accelerated;

(b) recording a potential trace output of the first electrode when applying the defined current density;

(c) applying a second defined current density or a defined potential to a substantially fully accelerated surface of a second electrode while in contact with the electroplating bath of interest,
  wherein the second defined current density or the defined potential represents the current density or potential experienced within a feature on the substrate when electroplated in the electroplating bath of interest;

(d) recording a second potential trace output and/or a current density trace output of the second electrode when applying the second defined current density or the defined potential; and (e) determining, based on information contained in one or more of the outputs, whether the additives of the electroplating bath of interest meet a defined electroplating specification.

23. A method of analyzing an electroplating bath of interest, the method comprising:

(a) applying a current to a first electrode while in contact with the electroplating bath of interest, wherein the first electrode's surface is not substantially fully accelerated;

(b) recording an electrical output of the first electrode produced in response to the applied current;

(c) applying a second current or a potential to a substantially fully accelerated surface of a second electrode while in contact with the electroplating bath of interest, (d) recording a second electrical output of the second electrode when applying the second current or the potential; and (e) determining, based on information contained in the outputs, whether the electroplating bath of interest meets a defined electroplating specification.

24. The method of claim 23, wherein the first and second electrodes are the same electrode with different surface metals deposited thereon.

* * * * *